(12) United States Patent
Cosgrove et al.

(10) Patent No.: US 10,877,039 B2
(45) Date of Patent: Dec. 29, 2020

(54) DIAGNOSTIC FOR COLORECTAL CANCER

(71) Applicant: VISION TECH BIO PTY. LTD., Melbourne (AU)

(72) Inventors: Leah Jane Cosgrove, Unley (AU); Bruce Tabor, Stanhope Gardens (AU); Antony Wilks Burgess, Camberwell (AU); Edouard Collins Nice, Docklands (AU)

(73) Assignee: VISION TECH BIO PTY. LTD., Melbourne (AU)

( * ) Notice: Subject to any disclaimer, the term of this patent is extended or adjusted under 35 U.S.C. 154(b) by 0 days.

(21) Appl. No.: 15/471,147

(22) Filed: Mar. 28, 2017

(65) Prior Publication Data

US 2017/0205414 A1 Jul. 20, 2017

Related U.S. Application Data

(63) Continuation of application No. 13/809,785, filed as application No. PCT/AU2011/000895 on Jul. 14, 2011, now abandoned.

(30) Foreign Application Priority Data

Jul. 14, 2010 (AU) ................ 2010903140

(51) Int. Cl.
*C12Q 1/6886* (2018.01)
*G01N 33/574* (2006.01)

(52) U.S. Cl.
CPC ..... *G01N 33/57419* (2013.01); *C12Q 1/6886* (2013.01); *G01N 33/57488* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | |
|---|---|---|
| 2008/0221056 A1 | 9/2008 | Baylin et al. |
| 2009/0017463 A1 | 1/2009 | Bhowmick |
| 2010/0111969 A1 | 5/2010 | Fricke et al. |
| 2013/0345322 A1 | 12/2013 | Cosgrove et al. |

FOREIGN PATENT DOCUMENTS

| | | |
|---|---|---|
| WO | WO 2005/029091 A2 | 3/2005 |
| WO | WO 2008/005469 A2 | 1/2008 |
| WO | WO 2008/073660 A1 | 6/2008 |
| WO | WO 2008/079269 A2 | 7/2008 |
| WO | WO 2005/116178 A2 | 9/2008 |
| WO | WO 2008/104380 A2 | 9/2008 |
| WO | WO 2008/116178 A2 | 9/2008 |
| WO | WO 2008/138522 A1 | 11/2008 |
| WO | WO 2008/144345 A2 | 11/2008 |
| WO | WO 2009/037572 A2 | 3/2009 |
| WO | WO2009037572 * | 3/2009 |
| WO | WO 2009/126543 A1 | 10/2009 |
| WO | WO 2010/065567 A2 | 6/2010 |
| WO | WO 2010/065940 A1 | 6/2010 |
| WO | WO 2010/096674 A2 | 8/2010 |
| WO | WO 2011/090516 A1 | 7/2011 |

OTHER PUBLICATIONS

Zitt et al (Disease Markers 24:101-109, 2008, IDS #32, filed on Nov. 13, 2017 (Year: 2000).*
Haug et al (British J Can, 96:1329-1334, 2007, IDS #31, filed on Nov. 13, 2017 (Year: 2007).*
Liou et al (J clin Endocrinol Metabl Apr. 2010, IDS #30, filed on Nov. 13, 2017 (Year: 2010).*
Untergasser et al (Int J Cancer 122: 1539-1547, 2008 (Year: 2008).*
Burgdorf et al (Acta Oncologica 48:1157-1164, 2009 (Year: 2009).*
Tonus et al, World J Gastroenterol 12:7007-7011 2006 (Year: 2006).*
International Search Report, dated Oct. 26, 2011 in connection with PCT International Application No. PCT/AU2011/000895, filed Jul. 14, 2011.
Written Opinion of the International Searching Authority, dated Oct. 26, 2011, in connection with PCT International Application No. PCT/AU2011/000895, filed Jul. 14, 2011.
International Preliminary Report on Patentability, dated Jan. 15, 2013, in connection with PCT International Application No. PCT/AU2011/000895, filed Jul. 14, 2011.
Supplementary European Search Report dated Jan. 3, 2014 in connection with European Application No. 11806149.8.
Ward et al., "Identification of serum biomarkers for colon cancer by proteomic analysis," British Journal of Cancer, 2006, 94:1898-1905.
Perez et al., "Serum Total Gangliosides and TA90-IC Levels: Novel Immunologic Markers in Colorectal Cancer," The Cancer Journal, Jan./Feb. 2002, 8(1):55-61.
Rubie et al., "Correlation of IL-8 with induction, progression and metastatic potential of colorectal cancer," World Journal of Gastroenterology, Oct. 7, 2007, 13(37):4996-5002.
Baler et al, Anticancer Research vol. 25:3581-3584, 2005.
Extended European Search Report and Written Opinion dated Apr. 13, 2015 in connection with European Application No. 14178981.8.
Liou et al., "Plasma insulin-like growth factor-binding protein-2 levels as diagnostic and prognostic biomarker of colorectal cancer," J. Clin. Endocrinol. Metab., Apr. 2010, 95(4) : 1717-1725.

(Continued)

*Primary Examiner* — Lei Yao
(74) *Attorney, Agent, or Firm* — Melissa Hunter-Ensor; Leslie Serunian; Greenberg Traurig, LLP

(57) ABSTRACT

The present invention provides a method for diagnosing or detecting colorectal cancer in a subject, the method comprising determining the presence and/or level of biomarkers selected from IL-8, IGFBP2, MAC2BP, M2PK, IL-13, DKK-3, EpCam, MIP1β, TGFβ1, and TIMP-1. The invention also relates to diagnostic kits comprising reagents for determining the presence and/or level of the biomarkers and methods of detecting or diagnosing colorectal cancer.

5 Claims, 11 Drawing Sheets

Figure 1:
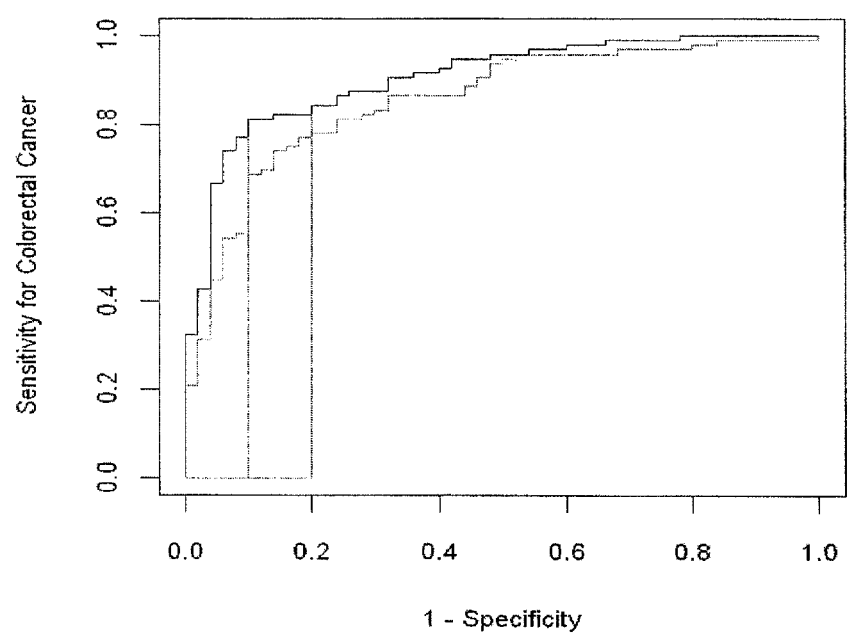

Specification includes a Sequence Listing.

(56) References Cited

OTHER PUBLICATIONS

Haug et al, British J Can, 96:1329-1334, 2007.
Zitt et al, Disease Markers 24: 101-109, 2008.
Office Action dated Jul. 28, 2015 in connection with Russian Patent Application No. 2013103995/15(005757) (English translation).
Wu et al., "Overexpression and elevated plasma level of tumor-associated antigen 90K/Mac-2 binding protein in colorectal carcinoma", Proteomics Clin. Appl., 2008, 2:1586-95.
Patent Examination Report No. 2, dated Sep. 25, 2015 in connection with Australia Patent Application No. 2011279555
English translation of Notice of Rejection dated Jan. 29, 2016 in connection with Japanese Patent Application No. 2013-518909.
Shastri et al., Prospective multicenter evaluation of fecal tumor pyruvate kinase type M2 (M2-PK) 'as a screening biomarker for colorectal neoplasia Int. J. Cancer: 119, 2651-2656 (2006).
Fung et al., (2015) Blood-Based Protein Biomarker Panel for the Detection of Colorectal Cancer. PLoS ONE 10(3): e0120425. doi:10.1371/journal.pone.0120425.
Autenshljus et al. (2009), Protivovospalitel' nye tsitokiny i antitela k nim prirake zheludochno-kishechnogo trakta, Sibirskij Onkologicheskij Zhurnal, 2009, Appendix No. 2, pp. 18-19; p. 19, col. 2, lines 1-10, including explanation of the relevance of the document in English.
Antolovi et al, BMC Biotechnology 10:35, Apr. 2010.
Burgdorf et al, Acta Oncologica, 48:1157-1164, 2009.
Todaro et al, Cell Stem cell, 1:389-4-2, 2007.
Lacovazzi et al, 32:160-164, 2010.

\* cited by examiner

'Useful' serum models (of 485) in which each biomarker appears

SEQUENCE LISTING

```
<160> NUMBER OF SEQ ID NOS: 14

<210> SEQ ID NO 1
<211> LENGTH: 99
<212> TYPE: PRT
<213> ORGANISM: Homo sapiens

<400> SEQUENCE: 1

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
        50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 2
<211> LENGTH: 328
<212> TYPE: PRT
<213> ORGANISM: Homo sapiens

<400> SEQUENCE: 2

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly Gly
                20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Val Ala Pro Pro
        50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
    130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190
```

```
Val Phe Arg Glu Lys Val Thr Glu Gln His Arg Gln Met Gly Lys Gly
            195                 200                 205

Gly Lys His His Leu Gly Leu Glu Glu Pro Lys Lys Leu Arg Pro Pro
210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
            245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
290                 295                 300

Gly Asp Pro Glu Cys His Leu Phe Tyr Asn Glu Gln Gln Glu Ala Arg
305                 310                 315                 320

Gly Val His Thr Gln Arg Met Gln
            325

<210> SEQ ID NO 3
<211> LENGTH: 585
<212> TYPE: PRT
<213> ORGANISM: Homo sapiens

<400> SEQUENCE: 3

Met Thr Pro Pro Arg Leu Phe Trp Val Trp Leu Leu Val Ala Gly Thr
1               5                   10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
            35                  40                  45

Cys Asp Asn Leu Trp Asp Leu Thr Asp Ala Ser Val Val Cys Arg Ala
50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
            85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
            115                 120                 125

Ser Thr His Thr Leu Asp Leu Ser Arg Glu Leu Ser Glu Ala Leu Gly
            130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
            165                 170                 175

Thr Ala Asn Leu Glu Ala Gln Ala Leu Trp Lys Glu Pro Gly Ser Asn
            180                 185                 190

Val Thr Met Ser Val Asp Ala Glu Cys Val Pro Met Val Arg Asp Leu
            195                 200                 205

Leu Arg Tyr Phe Tyr Ser Arg Arg Ile Asp Ile Thr Leu Ser Ser Val
            210                 215                 220

Lys Cys Phe His Lys Leu Ala Ser Ala Tyr Gly Ala Arg Gln Leu Gln
```

-continued

```
                225                 230                 235                 240
Gly Tyr Cys Ala Ser Leu Phe Ala Ile Leu Leu Pro Gln Asp Pro Ser
                245                 250                 255

Phe Gln Met Pro Leu Asp Leu Tyr Ala Tyr Ala Val Ala Thr Gly Asp
                260                 265                 270

Ala Leu Leu Glu Lys Leu Cys Leu Gln Phe Leu Ala Trp Asn Phe Glu
                275                 280                 285

Ala Leu Thr Gln Ala Glu Ala Trp Pro Ser Val Pro Thr Asp Leu Leu
                290                 295                 300

Gln Leu Leu Leu Pro Arg Ser Asp Leu Ala Val Pro Ser Glu Leu Ala
305                 310                 315                 320

Leu Leu Lys Ala Val Asp Thr Trp Ser Trp Gly Glu Arg Ala Ser His
                325                 330                 335

Glu Glu Val Glu Gly Leu Val Glu Lys Ile Arg Phe Pro Met Met Leu
                340                 345                 350

Pro Glu Glu Leu Phe Glu Leu Gln Phe Asn Leu Ser Leu Tyr Trp Ser
                355                 360                 365

His Glu Ala Leu Phe Gln Lys Lys Thr Leu Gln Ala Leu Glu Phe His
                370                 375                 380

Thr Val Pro Phe Gln Leu Leu Ala Arg Tyr Lys Gly Leu Asn Leu Thr
385                 390                 395                 400

Glu Asp Thr Tyr Lys Pro Arg Ile Tyr Thr Ser Pro Thr Trp Ser Ala
                405                 410                 415

Phe Val Thr Asp Ser Ser Trp Ser Ala Arg Lys Ser Gln Leu Val Tyr
                420                 425                 430

Gln Ser Arg Arg Gly Pro Leu Val Lys Tyr Ser Ser Asp Tyr Phe Gln
                435                 440                 445

Ala Pro Ser Asp Tyr Arg Tyr Tyr Pro Tyr Gln Ser Phe Gln Thr Pro
                450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
                485                 490                 495

Ser Ser Asp Glu Leu Pro Val Leu Gly Leu Thr Lys Ser Gly Gly Ser
                500                 505                 510

Asp Arg Thr Ile Ala Tyr Glu Asn Lys Ala Leu Met Leu Cys Glu Gly
                515                 520                 525

Leu Phe Val Ala Asp Val Thr Asp Phe Glu Gly Trp Lys Ala Ala Ile
                530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
                565                 570                 575

Tyr Leu Thr Asn Ser Ser Gly Val Asp
                580                 585

<210> SEQ ID NO 4
<211> LENGTH: 531
<212> TYPE: PRT
<213> ORGANISM: Homo sapiens

<400> SEQUENCE: 4

Met Ser Lys Pro His Ser Glu Ala Gly Thr Ala Phe Ile Gln Thr Gln
1               5                   10                  15
```

```
Gln Leu His Ala Ala Met Ala Asp Thr Phe Leu Glu His Met Cys Arg
                 20                  25                  30

Leu Asp Ile Asp Ser Pro Pro Ile Thr Ala Arg Asn Thr Gly Ile Ile
             35                  40                  45

Cys Thr Ile Gly Pro Ala Ser Arg Ser Val Glu Thr Leu Lys Glu Met
 50                  55                  60

Ile Lys Ser Gly Met Asn Val Ala Arg Leu Asn Phe Ser His Gly Thr
 65                  70                  75                  80

His Glu Tyr His Ala Glu Thr Ile Lys Asn Val Arg Thr Ala Thr Glu
                 85                  90                  95

Ser Phe Ala Ser Asp Pro Ile Leu Tyr Arg Pro Val Ala Val Ala Leu
                100                 105                 110

Asp Thr Lys Gly Pro Glu Ile Arg Thr Gly Leu Ile Lys Gly Ser Gly
            115                 120                 125

Thr Ala Glu Val Glu Leu Lys Lys Gly Ala Thr Leu Lys Ile Thr Leu
130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
                180                 185                 190

Leu Val Thr Glu Val Glu Asn Gly Gly Ser Leu Gly Ser Lys Lys Gly
            195                 200                 205

Val Asn Leu Pro Gly Ala Ala Val Asp Leu Pro Ala Val Ser Glu Lys
210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
            275                 280                 285

Gly Ile Met Val Ala Arg Gly Asp Leu Gly Ile Glu Ile Pro Ala Glu
290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
            355                 360                 365

Asp Tyr Pro Leu Glu Ala Val Arg Met Gln His Leu Ile Ala Arg Glu
370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
                405                 410                 415

Val Glu Ala Ser Phe Lys Cys Cys Ser Gly Ala Ile Ile Val Leu Thr
            420                 425                 430

Lys Ser Gly Arg Ser Ala His Gln Val Ala Arg Tyr Arg Pro Arg Ala
```

```
                435                 440                 445
Pro Ile Ile Ala Val Thr Arg Asn Pro Gln Thr Ala Arg Gln Ala His
    450                 455                 460
Leu Tyr Arg Gly Ile Phe Pro Val Leu Cys Lys Asp Pro Val Gln Glu
465                 470                 475                 480
Ala Trp Ala Glu Asp Val Asp Leu Arg Val Asn Phe Ala Met Asn Val
                485                 490                 495
Gly Lys Ala Arg Gly Phe Phe Lys Lys Gly Asp Val Val Ile Val Leu
                500                 505                 510
Thr Gly Trp Arg Pro Gly Ser Gly Phe Thr Asn Thr Met Arg Val Val
                515                 520                 525
Pro Val Pro
    530

<210> SEQ ID NO 5
<211> LENGTH: 531
<212> TYPE: PRT
<213> ORGANISM: Homo sapiens

<400> SEQUENCE: 5

Met Ser Lys Pro His Ser Glu Ala Gly Thr Ala Phe Ile Gln Thr Gln
1               5                   10                  15
Gln Leu His Ala Ala Met Ala Asp Thr Phe Leu Glu His Met Cys Arg
            20                  25                  30
Leu Asp Ile Asp Ser Pro Pro Ile Thr Ala Arg Asn Thr Gly Ile Ile
        35                  40                  45
Cys Thr Ile Gly Pro Ala Ser Arg Ser Val Glu Thr Leu Lys Glu Met
    50                  55                  60
Ile Lys Ser Gly Met Asn Val Ala Arg Leu Asn Phe Ser His Gly Thr
65              70                  75                  80
His Glu Tyr His Ala Glu Thr Ile Lys Asn Val Arg Thr Ala Thr Glu
                85                  90                  95
Ser Phe Ala Ser Asp Pro Ile Leu Tyr Arg Pro Val Ala Val Ala Leu
            100                 105                 110
Asp Thr Lys Gly Pro Glu Ile Arg Thr Gly Leu Ile Lys Gly Ser Gly
        115                 120                 125
Thr Ala Glu Val Glu Leu Lys Lys Gly Ala Thr Leu Lys Ile Thr Leu
    130                 135                 140
Asp Asn Ala Tyr Met Glu Lys Cys Asp Glu Asn Ile Leu Trp Leu Asp
145                 150                 155                 160
Tyr Lys Asn Ile Cys Lys Val Val Glu Val Gly Ser Lys Ile Tyr Val
                165                 170                 175
Asp Asp Gly Leu Ile Ser Leu Gln Val Lys Gln Lys Gly Ala Asp Phe
            180                 185                 190
Leu Val Thr Glu Val Glu Asn Gly Gly Ser Leu Gly Ser Lys Lys Gly
        195                 200                 205
Val Asn Leu Pro Gly Ala Ala Val Asp Leu Pro Ala Val Ser Glu Lys
    210                 215                 220
Asp Ile Gln Asp Leu Lys Phe Gly Val Glu Gln Asp Val Asp Met Val
225                 230                 235                 240
Phe Ala Ser Phe Ile Arg Lys Ala Ser Asp Val His Glu Val Arg Lys
                245                 250                 255
Val Leu Gly Glu Lys Gly Lys Asn Ile Lys Ile Ile Ser Lys Ile Glu
            260                 265                 270
```

```
Asn His Glu Gly Val Arg Arg Phe Asp Glu Ile Leu Glu Ala Ser Asp
            275                 280                 285

Gly Ile Met Val Ala Arg Gly Asp Leu Gly Ile Glu Ile Pro Ala Glu
290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
                340                 345                 350

Leu Asp Gly Ala Asp Cys Ile Met Leu Ser Gly Glu Thr Ala Lys Gly
            355                 360                 365

Asp Tyr Pro Leu Glu Ala Val Arg Met Gln His Leu Ile Ala Arg Glu
        370                 375                 380

Ala Glu Ala Ala Met Phe His Arg Lys Leu Phe Glu Glu Leu Val Arg
385                 390                 395                 400

Ala Ser Ser His Ser Thr Asp Leu Met Glu Ala Met Ala Met Gly Ser
                405                 410                 415

Val Glu Ala Ser Tyr Lys Cys Leu Ala Ala Ala Leu Ile Val Leu Thr
                420                 425                 430

Glu Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
        450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
                515                 520                 525

Pro Val Pro
    530

<210> SEQ ID NO 6
<211> LENGTH: 531
<212> TYPE: PRT
<213> ORGANISM: Homo sapiens

<400> SEQUENCE: 6

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110
```

```
Asp Thr Lys Gly Pro Glu Ile Arg Thr Gly Leu Ile Lys Gly Ser Gly
            115                 120                 125

Thr Ala Glu Val Glu Leu Lys Lys Gly Ala Thr Leu Lys Ile Thr Leu
        130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
        355                 360                 365

Asp Tyr Pro Leu Glu Ala Val Arg Met Gln His Leu Ile Ala Arg Glu
    370                 375                 380

Ala Glu Ala Ala Met Phe His Arg Lys Leu Phe Glu Glu Leu Val Arg
385                 390                 395                 400

Ala Ser Ser His Ser Thr Asp Leu Met Glu Ala Met Ala Met Gly Ser
                405                 410                 415

Val Glu Ala Ser Tyr Lys Cys Leu Ala Ala Ala Leu Ile Val Leu Thr
            420                 425                 430

Glu Ser Gly Arg Ser Ala His Gln Val Ala Arg Tyr Arg Pro Arg Ala
        435                 440                 445

Pro Ile Ile Ala Val Thr Arg Asn Pro Gln Thr Ala Arg Gln Ala His
    450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
        515                 520                 525
```

Pro Val Pro
    530

<210> SEQ ID NO 7
<211> LENGTH: 146
<212> TYPE: PRT
<213> ORGANISM: Homo sapiens

<400> SEQUENCE: 7

Met His Pro Leu Leu Asn Pro Leu Leu Ala Leu Gly Leu Met Ala
1               5                   10                  15

Leu Leu Leu Thr Thr Val Ile Ala Leu Thr Cys Leu Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Gln
    130                 135                 140

Phe Asn
145

<210> SEQ ID NO 8
<211> LENGTH: 350
<212> TYPE: PRT
<213> ORGANISM: Homo sapiens

<400> SEQUENCE: 8

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

```
Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Arg Glu
                325                 330                 335

Pro Ala Ala Ala Ala Ala Leu Leu Gly Gly Glu Glu Ile
            340                 345                 350

<210> SEQ ID NO 9
<211> LENGTH: 350
<212> TYPE: PRT
<213> ORGANISM: Homo sapiens

<400> SEQUENCE: 9

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Ala Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190
```

```
Gly His Cys Thr Lys Met Ala Thr Arg Gly Ser Asn Gly Thr Ile Cys
            195                 200                 205

Asp Asn Gln Arg Asp Cys Gln Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Arg Glu
                325                 330                 335

Pro Ala Ala Ala Ala Ala Leu Leu Gly Gly Glu Glu Ile
            340                 345                 350

<210> SEQ ID NO 10
<211> LENGTH: 350
<212> TYPE: PRT
<213> ORGANISM: Homo sapiens

<400> SEQUENCE: 10

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220
```

```
            210                 215                 220
Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
                275                 280                 285

Val Gly Ser Arg Asp Gln Asp Gly Glu Ile Leu Leu Pro Arg Glu Val
            290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Met Ala Leu Arg Glu
                325                 330                 335

Pro Ala Ala Ala Ala Ala Leu Leu Gly Gly Glu Glu Ile
            340                 345                 350

<210> SEQ ID NO 11
<211> LENGTH: 314
<212> TYPE: PRT
<213> ORGANISM: Homo sapiens

<400> SEQUENCE: 11

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Asn Arg Gln Cys Gln Cys
            35                  40                  45

Thr Ser Val Gly Ala Gln Asn Thr Val Ile Cys Ser Lys Leu Ala Ala
        50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
                150                 155                 160
145

Ser Leu Arg Thr Ala Leu Gln Lys Glu Ile Thr Thr Arg Tyr Gln Leu
            165                 170                 175

Asp Pro Lys Phe Ile Thr Ser Ile Leu Tyr Glu Asn Asn Val Ile Thr
        180                 185                 190

Ile Asp Leu Val Gln Asn Ser Ser Gln Lys Thr Gln Asn Asp Val Asp
    195                 200                 205

Ile Ala Asp Val Ala Tyr Tyr Phe Glu Lys Asp Val Lys Gly Glu Ser
        210                 215                 220

Leu Phe His Ser Lys Lys Met Asp Leu Thr Val Asn Gly Glu Gln Leu
225                 230                 235                 240
```

```
Asp Leu Asp Pro Gly Gln Thr Leu Ile Tyr Tyr Val Asp Glu Lys Ala
            245                 250                 255

Pro Glu Phe Ser Met Gln Gly Leu Lys Ala Gly Val Ile Ala Val Ile
        260                 265                 270

Val Val Val Val Ile Ala Val Ala Gly Ile Val Val Leu Val Ile
        275                 280                 285

Ser Arg Lys Lys Arg Met Ala Lys Tyr Glu Lys Ala Glu Ile Lys Glu
290                 295                 300

Met Gly Glu Met His Arg Glu Leu Asn Ala
305                 310

<210> SEQ ID NO 12
<211> LENGTH: 92
<212> TYPE: PRT
<213> ORGANISM: Homo sapiens

<400> SEQUENCE: 12

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
            20                  25                  30

Ala Cys Cys Phe Ser Tyr Thr Ala Arg Lys Leu Pro Arg Asn Phe Val
        35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 13
<211> LENGTH: 390
<212> TYPE: PRT
<213> ORGANISM: Homo sapiens

<400> SEQUENCE: 13

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160
```

```
Lys Leu Lys Val Glu Gln His Val Glu Leu Tyr Gln Lys Tyr Ser Asn
            165                 170                 175

Asn Ser Trp Arg Tyr Leu Ser Asn Arg Leu Leu Ala Pro Ser Asp Ser
        180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
                260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
370                 375                 380

Arg Ser Cys Lys Cys Ser
385                 390

<210> SEQ ID NO 14
<211> LENGTH: 207
<212> TYPE: PRT
<213> ORGANISM: Homo sapiens

<400> SEQUENCE: 14

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140
```

```
Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205
```

DIAGNOSTIC FOR COLORECTAL CANCER

CROSS-REFERENCE TO RELATED APPLICATIONS

This application is continuation of U.S. Ser. No. 13/809,785, which is a § 371 national stage of PCT International Application No. PCT/AU2011/000895, filed Jul. 14, 2011, claiming priority of Australian Patent Application No. 2010903140, filed Jul. 14, 2010, the contents of each of which are hereby incorporated by reference in their entirety.

REFERENCE TO SEQUENCE LISTING

This application incorporates-by-reference nucleotide and/or amino acid sequences which are present in the file named "170328 84809 A Substitute Sequence Listing DH.txt," which is 41.2 kilobytes in size, and which was created Mar. 27, 2017 in the IBM-PC machine format, having an operating system compatibility with MS-Windows, which is contained in the text file filed Mar. 28, 2017 as part of this application.

FIELD OF THE INVENTION

The present invention relates to determining the presence and/or level of biomarkers for detecting or diagnosing colorectal cancer. The invention also relates to diagnostic kits comprising reagents for determining the presence and/or level of the biomarkers and methods of detecting or diagnosing colorectal cancer.

BACKGROUND OF THE INVENTION

Colorectal cancer, also referred to as colon cancer or bowel cancer, is the second most common cause of cancer worldwide. There is an annual incidence of almost a million colorectal cancer cases with an annual mortality around 500,000 (Cancer in Australia: an overview, 2008). Unfortunately, 30-50% of patients have occult or overt metastases at presentation and once tumours have metastasized prognosis is very poor with a five year survival of less than 10% (Etzioni et al., 2003). By contrast, greater than 90% of patients who present while the tumour is still localised will still be alive after 5 years and can be considered cured. The early detection of colorectal lesions would therefore significantly reduce the impact of colon cancer (Etzioni et al., 2003).

The current screening assays in widespread use for the diagnosis of colorectal cancer are the faecal occult blood test (FOBT), flexible sigmoidoscopy, and colonoscopy (Lieberman, 2010). FOBT has relatively low specificity resulting in a high rate of false positives. All positive FOBT must therefore be followed up with colonoscopy. Sampling is done by individuals at home and requires at least two consecutive faecal samples to be analysed to achieve optimal sensitivity. Some versions of the FOBT also require dietary restrictions prior to sampling. FOBT also lacks sensitivity for early stage cancerous lesions that do not bleed into the bowel and as stated above, these are the lesions for which treatment is most successful.

While FOBT screening does result in reduction of mortality due to colorectal cancer it suffers from a low compliance rate (30-40%), most likely due to the unpalatable nature of the test, which limits its usefulness as a screening tool. Colonoscopy is the current gold standard and has a specificity of greater then 90% but it is intrusive and costly with a small but finite risk of complications (2.1 per 1000 procedures) (Levin, 2004). Development of a rapid, specific, cheap blood based assay would overcome compliance issues commonly seen with other screening tests (Tonus, 2006; Hundt et al., 2007) and would be more acceptable as part of a large screening assay.

SUMMARY OF THE INVENTION

The present inventors investigated over sixty biomarkers associated with colorectal cancer, but found that none of the biomarkers alone would be suitable as a diagnostic test. Surprisingly, it was found that determining the presence and/or level of at least two biomarkers associated with colorectal cancer in a sample from a subject allowed for the detection or diagnosis of colorectal cancer at any of the stages of disease. Determining the presence and/or level of at least two biomarkers advantageously provides a diagnostic test that is at least comparable in sensitivity and specificity to the FOBT.

Accordingly, in one aspect, the present invention provides a method for diagnosing or detecting colorectal cancer in a subject, the method comprising:
  i) determining the presence and/or level of at least two biomarkers selected from IL-8, IGFBP2, MAC2BP, M2PK, IL-13, DKK-3, EpCam, MIP1β, TGFβ1, and TIMP-1 in a sample from the subject,
  wherein the presence and/or level of the two biomarkers is indicative of colorectal cancer.

In one embodiment, the method comprises determining the presence and/or level of two biomarkers selected from M2PK, EpCam, IL-13, DKK-3, IL-8 and IGFBP2.

In another embodiment, the method comprises determining the presence and/or level of expression of at least three of the biomarkers.

In one embodiment, the three biomarkers are selected from M2PK, EpCam, IL-13, DKK-3, IL-8, IGFBP2, MIP1β, TGFβ1 and MAC2BP.

In one particular embodiment, the method comprises determining the presence and/or level of three biomarkers, wherein the three biomarkers are:
  i) DKK-3, M2PK, and IGFBP2;
  ii) M2PK, IGFBP2, and EpCAM;
  iii) M2PK, MIP1β, and TGFβ1; or
  iv) IL-8, IL-13, and MAC2BP.

In another embodiment, the method comprises determining the presence and/or level of expression of at least four of the biomarkers.

In one particular embodiment, the method comprises determining the presence and/or level of four biomarkers, wherein the four biomarkers are:
  i) DKK-3, M2PK, MAC2BP, and IGFBP2;
  ii) IL-8, IL-13, MAC2BP, and EpCam;
  iii) DKK3, M2PK, TGFβ1, and TIMP-1;
  iv) M2PK, MIP1β, IL-13, and TIMP-1; or
  v) IL-8, MAC2BP, IGFBP2, and EpCam.

In yet another embodiment, the method comprises determining the presence and/or level of at least five of the biomarkers.

In one particular embodiment, the five biomarkers are IL-8, IGFBP2, MAC2BP, M2PK, and IL-13.

In another embodiment, the method comprises determining the presence and/or level of at least six of the biomarkers.

In another embodiment, the method comprises determining the presence and/or level of at least seven of the biomarkers.

In one particular embodiment, the seven biomarkers are:

i) IL-8, IGFBP2, MAC2BP, M2PK, IL-13, DKK-3, and TGFβ1; or ii) IL-8, IGFBP2, MAC2BP, M2PK, IL-13, EpCam, and MIP1β.

In yet another embodiment, the method comprises determining the presence and/or level of at least eight of the biomarkers.

In one embodiment, the method comprises determining the presence and/or level of at least nine of the biomarkers.

In yet another embodiment, the method comprises determining the presence and/or level of at least ten of the biomarkers.

In another embodiment, the method comprises determining the presence and/or level of a combination of biomarkers as provided in any of Tables 7 to 18.

In another embodiment, the method comprises detecting the presence and/or level of least one additional biomarker selected from IGF-I, IGF-II, IGF-BP2, Amphiregulin, VEGFA, VEGFD, MMP-1, MMP-2, MMP-3, MMP-7, MMP-9, TIMP-1, TIMP-2, ENA-78, MCP-1, MIP-1β, IFN-γ, IL-10, IL-13, IL-1β, IL-4, IL-8, IL-6, MAC2BP, Tumor M2 pyruvate kinase, M65, OPN, DKK-3, EpCam, TGFβ-1, and VEGFpan.

In one embodiment, the method diagnoses or detects colorectal cancer with a sensitivity of at least 50%.

In another embodiment, the method diagnoses or detects colorectal cancer with a sensitivity of at least 66%.

In yet another embodiment, the method diagnoses or detects colorectal cancer with a sensitivity of at least 77%.

In one embodiment, the method diagnoses or detects colorectal cancer with a specificity of at least 75%.

In one embodiment, the method diagnoses or detects colorectal cancer with a specificity of at least 80%.

In another embodiment, the method diagnoses or detects colorectal cancer with a specificity of at least 90%.

In yet another embodiment, the method diagnoses or detects colorectal cancer with a specificity of at least 95%.

In another embodiment, the method diagnoses or detects Dukes Stage A colorectal cancer with a sensitivity of at least 50% and a specificity of at least 95%.

In yet another embodiment, the method diagnoses or detects Dukes Stage A colorectal cancer with a sensitivity of at least 60% and a specificity of at least 80%.

In another embodiment, the method diagnoses or detects Dukes Stage A colorectal cancer with a sensitivity of at least 50% and a specificity of at least 90%.

The skilled person will understand that Dukes Stage A corresponds to TNM Classifications T1, N0, M0 and T2, N0, M0.

Thus in one embodiment, the method diagnoses or detects TNM Classification T1, N0, M0 or T2, N0, M0 colorectal cancer with a sensitivity of at least 50% and a specificity of at least 95%.

In yet another embodiment, the method diagnoses or detects TNM Classification T1, N0, M0 or T2, N0, M0 colorectal cancer with a sensitivity of at least 60% and a specificity of at least 80%.

In another embodiment, the method diagnoses or detects TNM Classification T1, N0, M0 or T2, N0, M0 colorectal cancer with a sensitivity of at least 50% and a specificity of at least 90%.

Any suitable technique for the detection of polypeptides may be used in the methods of the invention. In one embodiment, the method comprises contacting the sample with at least one compound that binds a biomarker polypeptide. Alternatively, the method comprises detecting the polypeptides by mass spectrometry.

In one particular embodiment, the compound is detectably labelled.

In another embodiment, the compound is an antibody.

In one embodiment, the compound is bound to a solid support.

In the methods of the invention, determining the presence and/or level of the biomarker may comprise determining the presence and/or level of a polynucleotide encoding the biomarker, such as a biomarker gene transcript. Thus, in one embodiment, the biomarkers are polynucleotides.

In yet another embodiment of the methods of the invention, the method comprises:

i) determining the presence and/or level of the biomarkers in the sample from the subject; and ii) comparing the presence and/or level of the biomarkers to a control, wherein a presence and/or level in the sample that is different to the control is indicative of colorectal cancer.

In one embodiment, the sample comprises blood, plasma, serum, urine, platelets, magakaryocytes or faeces.

In another aspect, the present invention provides a method of treatment comprising:

(i) diagnosing or detecting colorectal cancer according to the method of the invention; and (ii) administering or recommending a therapeutic for the treatment of colorectal cancer.

In yet another aspect, the present invention provides a method for monitoring the efficacy of treatment of colorectal cancer in a subject, the method comprising treating the subject for colorectal cancer and then detecting the presence and/or level of at least two biomarkers selected from IL-8, IGFBP2, MAC2BP, M2PK, IL-13, DKK-3, EpCam, MIP1β, TGFβ1, and TIMP-1 in a sample from the subject, wherein an absence of and/or reduction in the level of expression of the polypeptides after treatment when compared to before treatment is indicative of effective treatment.

In another aspect, the present invention provides an array of at least two compounds for the diagnosis or detection of colorectal cancer, wherein each of the compounds binds a different biomarker polypeptide selected from IL-8, IGFBP2, MAC2BP, M2PK, IL-13, DKK-3, EpCam, MIP1β, TGFβ1, and TIMP-1.

In yet another aspect, the present invention provides a kit for diagnosing or detecting colorectal cancer in a subject, the kit comprising two compounds that each binds a different biomarker polypeptide selected from IL-8, IGFBP2, MAC2BP, M2PK, IL-13, DKK-3, EpCam, MIP1β, TGFβ1, and TIMP-1.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As will be apparent, preferred features and characteristics of one aspect of the invention are applicable to many other aspects of the invention.

The invention is hereinafter described by way of the following non-limiting Examples and with reference to the accompanying figures.

BRIEF DESCRIPTION OF THE ACCOMPANYING DRAWINGS

FIG. 1. In Study 3 an optimum combination of the 46 potential protein biomarkers was found using logistic regression modelling, resulting in a panel of seven biomarkers and is illustrated as a ROC curve (black curve). The performance of this "panel" on independent data was estimated using "leave one out" cross-validation (grey curve). The vertical lines are drawn at points of 80% and 90% specificity—operating points of interest in screening tests. Performance statistics are given in Table 5.

Figure 2:
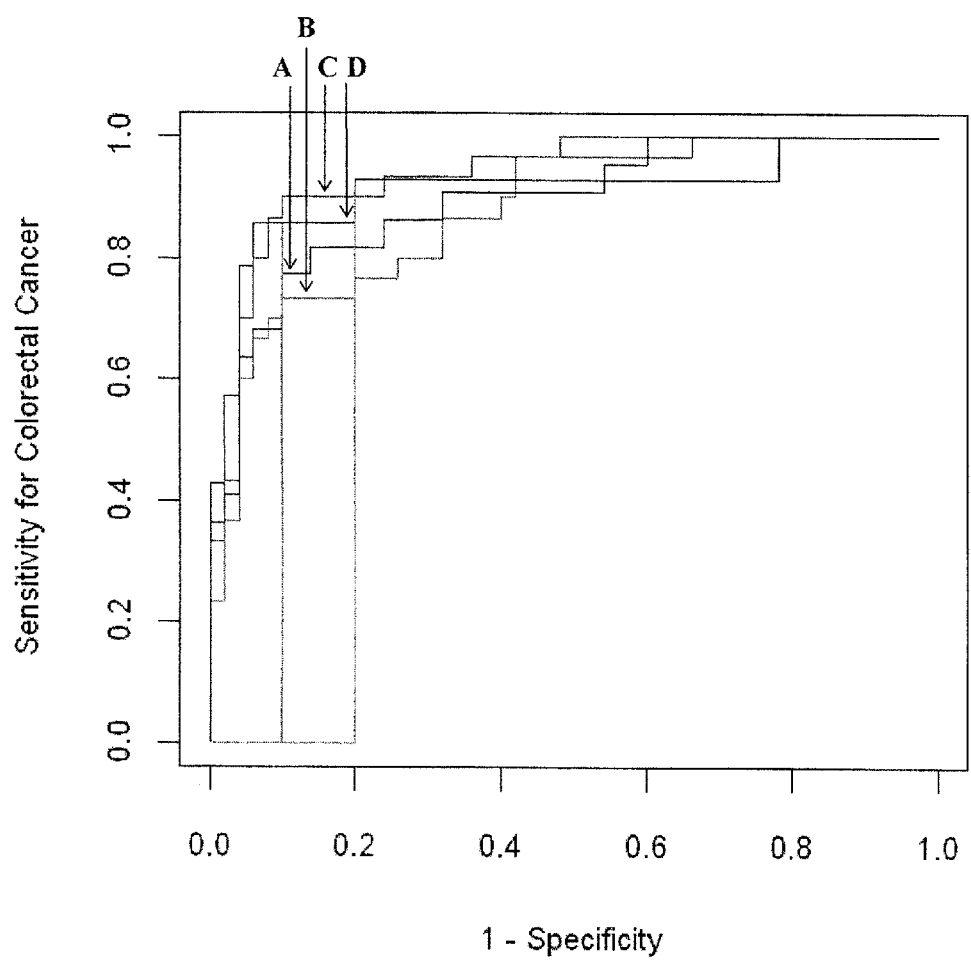

FIG. 2. Performance of a seven biomarker model identifying colorectal cancer patients from normals at each Dukes Stage illustrated by ROC curves for each stage. A (red)—Stage A, B (green)—Stage B, C (blue)—Stage C, and D (black)—Stage D from Study 3a. Performance characteristics are given in Table 6.

Figure 3:
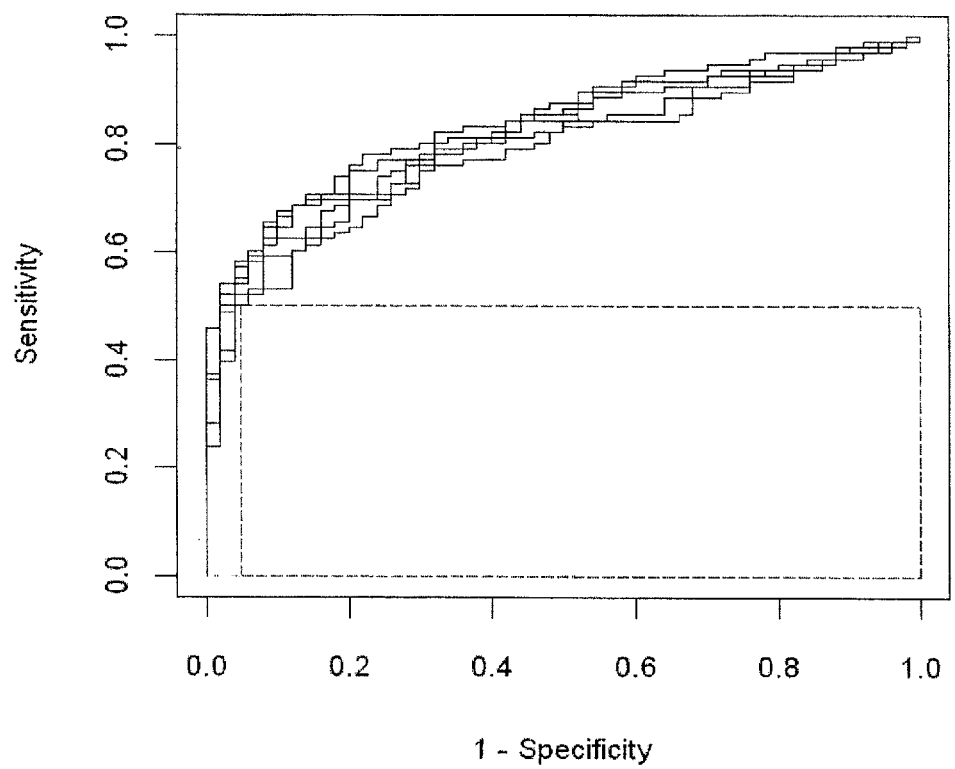

FIG. 3. When biomarker results from Study 4 (also referred to as Study 3 remeasured) were modelled in pairs a total of 5 pairs (out of a possible 45 combinations selected from the list of 10 biomarkers above) could be shown to produce a sensitivity above 52% at a specificity of 95. The performance of these pair wise biomarker combinations is illustrated as ROC curves (n=5 curves). Performance characteristics are given in Table 7.

Figure 4:
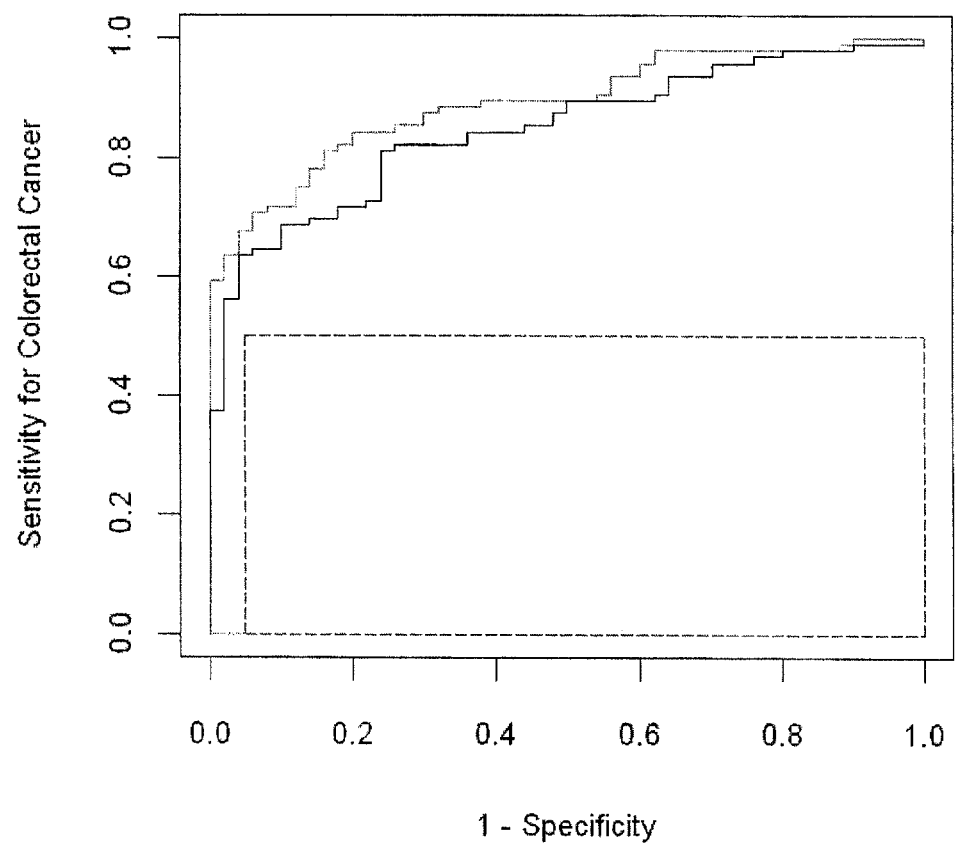

FIG. 4. An example of a 3 biomarker model generated from Study 4 data which had a sensitivity of at least 50% at 95% specificity. There were 968 possible 3-10 biomarker combinations and approximately half of those combinations showed a performance of at least 50% sensitivity at 90% specificity.

Figure 5:
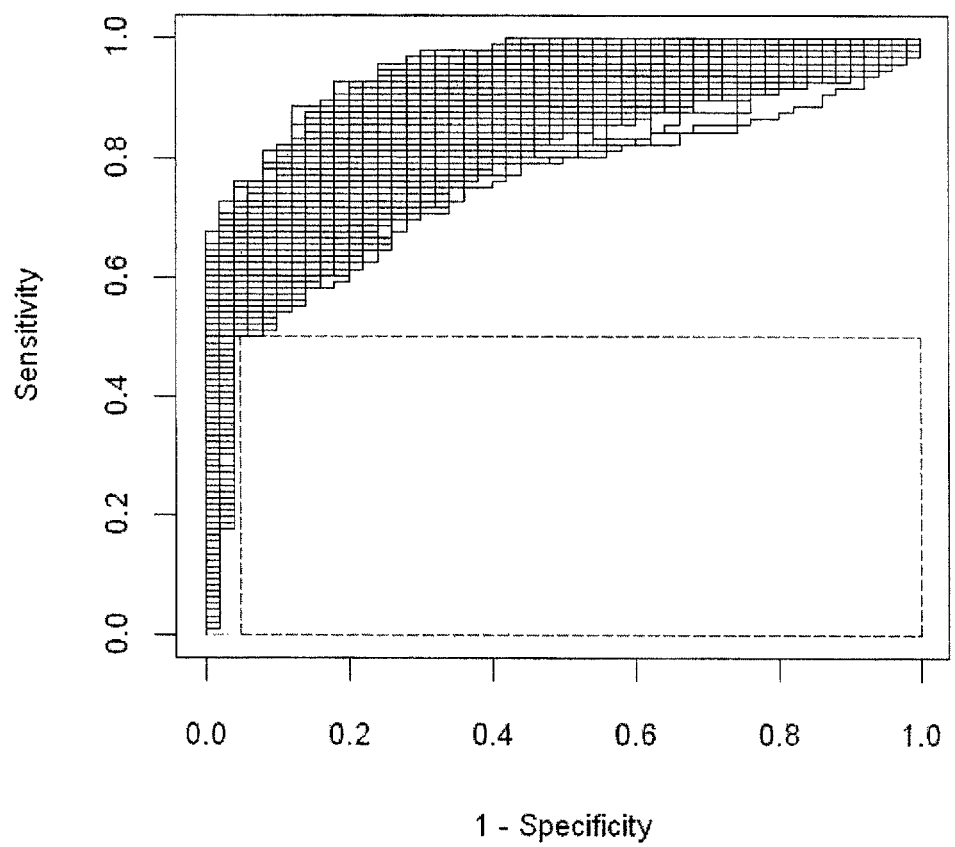

FIG. 5. ROC curves are illustrated for all combinations of 3-10 biomarkers generated from Study 4 data which have a sensitivity of at least 50% at 95% specificity (n=485 cross validated curves out of a possible 968 models).

Figure 6:
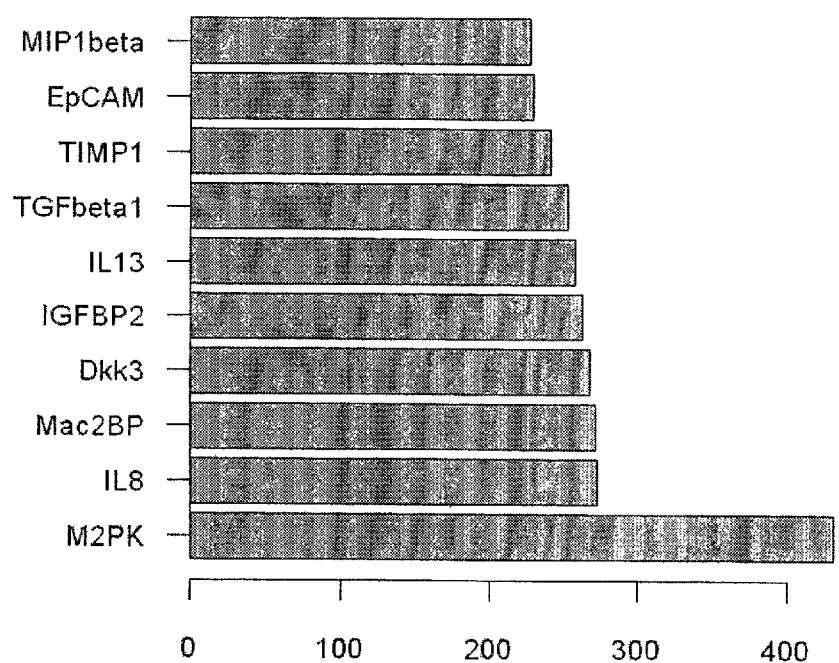

FIG. 6. Frequency of each biomarker in the best 485 models. These BMs represent all serum models that gave a sensitivity of at least 50% at 95% The high representation of all 10 biomarkers in the useful models demonstrates the unity of our selection of these 10 biomarkers.

Figure 7:
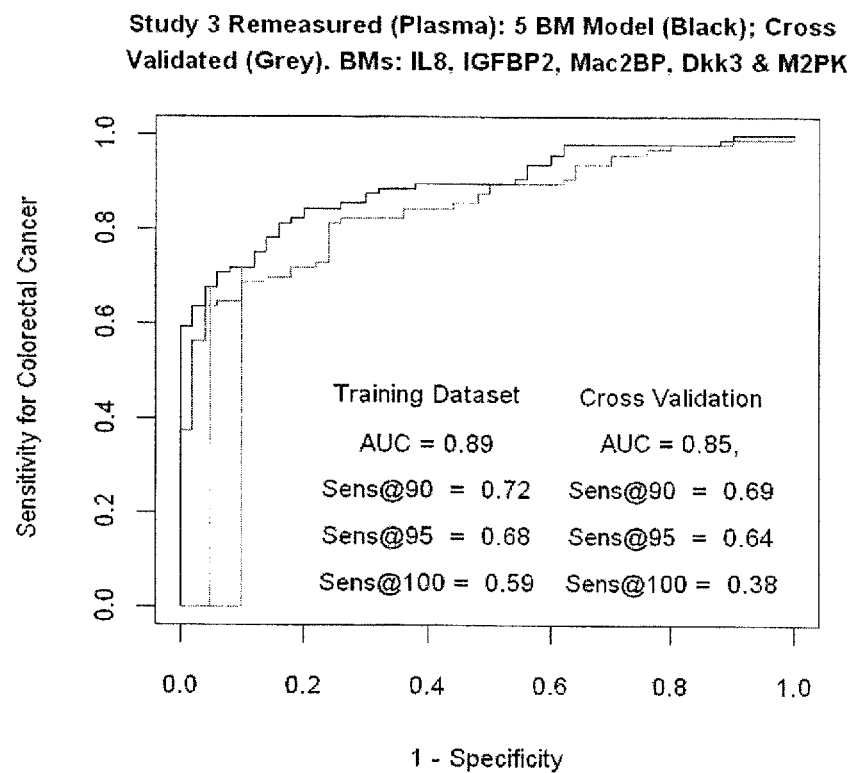

FIG. 7. A 5 biomarker model generated from Study 4 data is illustrated as a ROC curve (black) and cross validated ROC curve (grey). This model shows a sensitivity of 68% at 95% specificity when all stages of disease are included and when cross validated gave a sensitivity of 64%. Biomarkers included are [IL-8, IGFBP2, Mac2BP, DKK-3 and M2PK].

Figure 8:
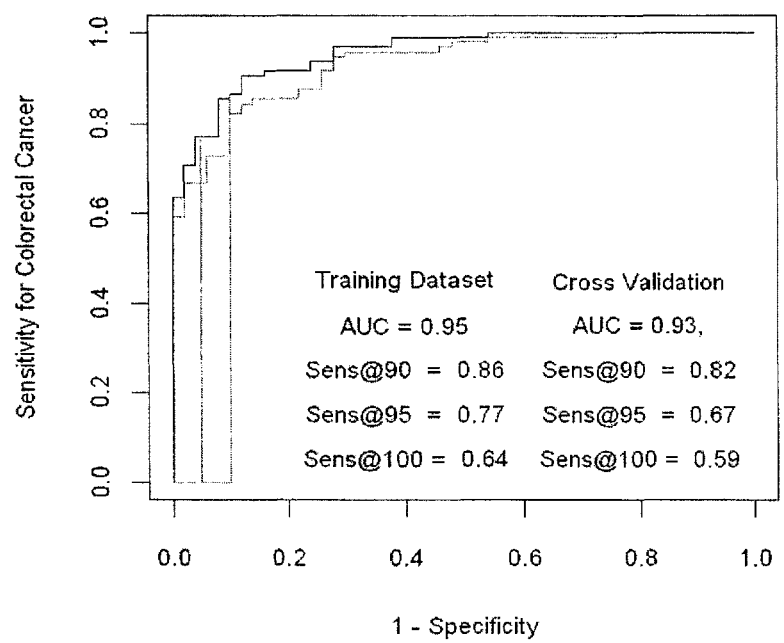

FIG. 8. A 6 biomarker model generated from Study 4 data is illustrated as a ROC curve (black) and cross validated ROC curve (Grey). This model shows a sensitivity of 77% at a specificity of 95% when all stages of disease are included and when cross validated gave a sensitivity of 67%. Biomarkers included are [IL-8, IGFBP2, Mac2BP, DKK-3, TGFbeta1&M2PK].

Figure 9:
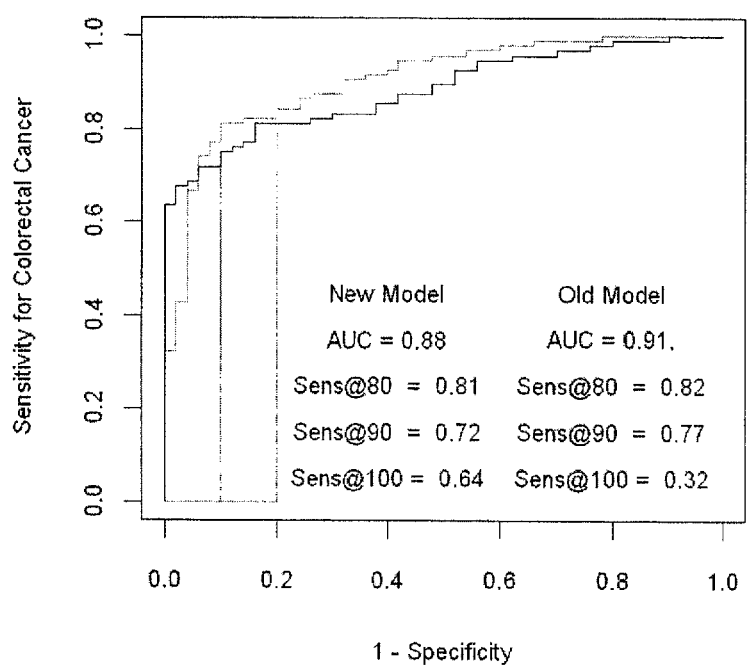

FIG. 9. Two alternative seven biomarker models generated from Study 3a data are shown. One was optimised for high specificity (black/new) and an alternative or model optimised for area under the curve is shown (grey/old). At 90% specificity the sensitivity was 72% for the new model and 77% for the older model. Biomarkers included were as follows:

New: IL8, IGFBP2, s90MAC2BP, M2PK, DKK-3, IL-13 & TGFbeta,

Old: IL8, IGFBP2, s90MAC2BP, M2PK, EpCAM, IL13 & MIP-1b.

Figure 10:
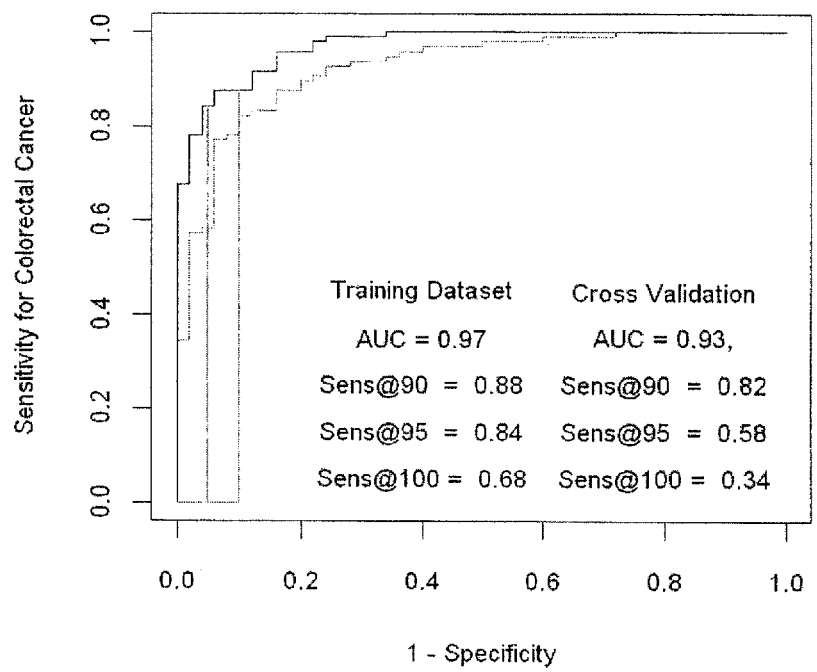

FIG. 10. A seven biomarker model generated from Study 4 data is illustrated as a ROC curve (black) and cross validated ROC curve (grey). This model shows, a sensitivity of 84% at a specificity of 95%. Biomarkers included are [M2PK serum, IL8.plasma, TGF beta1.serum, IGFBP2.plasma, Mac2BP.serum, TIMP1.plasma and Dkk3 plasma.

Figure 11:
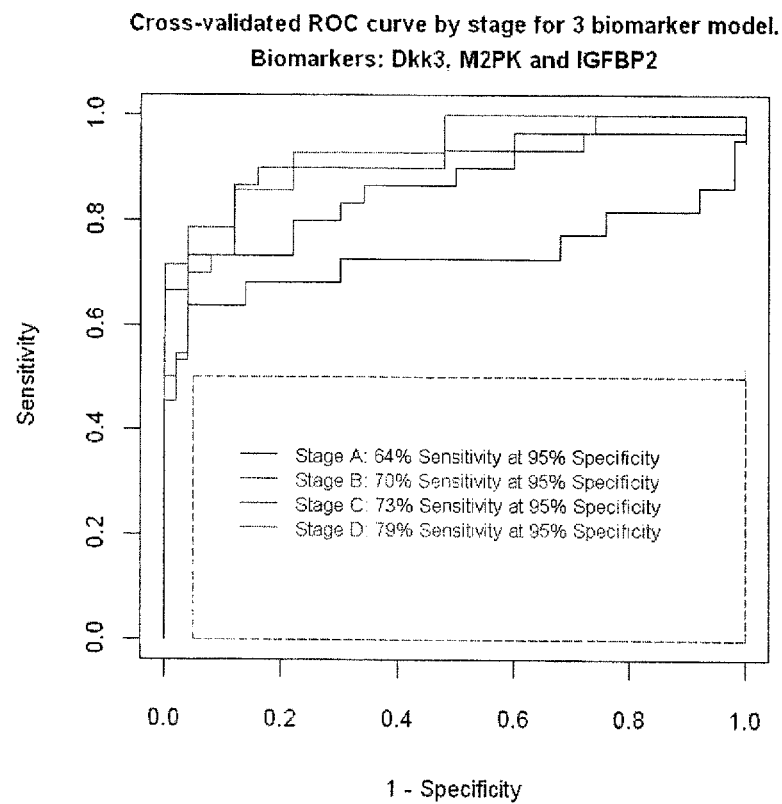

FIG. 11. Cross validated ROC curves showing the performance of a 3 biomarker model for each Dukes stage is illustrated. This data demonstrates the validity of the choice of three biomarkers (DKK-3, M2PK and IGFBP2) for detecting cancer at different stages of the disease progression. The data indicates that at Stage A if the three markers are used, the test still will achieve a significant sensitivity of 64% at 95% specificity which is comparable to the sensitivity achieved at late stage disease (79%). That is the biomarker panel of three will pick up early disease states allowing early detection. Biomarkers included are Dkk3, M2PK and IGFBP2.

KEY TO THE SEQUENCE LISTING

SEQ ID NO:1—amino acid sequence of IL-8
SEQ ID NO:2—amino acid sequence of IGFBP2
SEQ ID NO:3—amino acid sequence of MAC2BP
SEQ ID NO:4—amino acid sequence of M2PK variant 1
SEQ ID NO:5—amino acid sequence of M2PK variant 2
SEQ ID NO:6—amino acid sequence of M2PK variant 3
SEQ ID NO:7—amino acid sequence of IL-13
SEQ ID NO:8—amino acid sequence of DKK-3 variant 1
SEQ ID NO:9—amino acid sequence of DKK-3 variant 2
SEQ ID NO: 10—amino acid sequence of DKK-3 variant 3
SEQ ID NO:11—amino acid sequence of EpCam
SEQ ID NO:12—amino acid sequence of MIP1β
SEQ ID NO:13—amino acid sequence of TGFβ1
SEQ ID NO:14—amino acid sequence of TIMP-1

DETAILED DESCRIPTION

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, $3^{rd}$ edn, Cold Spring Harbour Laboratory Press (2001), R. Scopes, Protein Purification—Principals and Practice, $3^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term "colorectal cancer", also known as "colon cancer", "bowel cancer" or "rectal cancer", refers to all forms of cancer originating from the epithelial cells lining the large intestine and/or rectum.

As used herein, "biomarker" refers to any molecule, such as a gene, gene transcript (for example mRNA), peptide or protein or fragment thereof produced by a subject which is useful in differentiating subjects having colorectal cancer from normal or healthy subjects.

As used herein, the term "diagnosis", and variants thereof such as, but not limited to, "diagnose", "diagnosed" or "diagnosing" shall not be limited to a primary diagnosis of a clinical state, but should be taken to include diagnosis of recurrent disease.

As used herein, the term "subject" refers to any animal that may develop colorectal cancer and includes animals such as mammals, e.g. humans, or non-human mammals such as cats and dogs, laboratory animals such as mice, rats, rabbits or guinea pigs, and livestock animals. In a preferred embodiment, the subject is a human.

The "sample" may be of any suitable type and may refer, e.g., to a material in which the presence or level of biomarkers can be detected. Preferably, the sample is obtained from the subject so that the detection of the presence and/or level of biomarkers may be performed in vitro. Alternatively, the presence and/or level of biomarkers can be detected in vivo. The sample can be used as obtained directly from the source or following at least one step of (partial) purification. The sample can be prepared in any convenient medium which does not interfere with the method of the invention. Typically, the sample is an aqueous solution, biological fluid, cells or tissue. Preferably, the sample is blood, plasma, serum, urine, platelets, megakaryocytes or faeces. Pre-treatment may involve, for example, preparing plasma from blood, diluting viscous fluids, and the like. Methods of treatment can involve filtration, distillation, separation, concentration, inactivation of interfering components, and the addition of reagents. The selection and pre-treatment of biological samples prior to testing is well known in the art and need not be described further.

As used herein the terms "treating", "treat" or "treatment" include administering a therapeutically effective amount of a compound sufficient to reduce or delay the onset or progression of colorectal cancer, or to reduce or eliminate at least one symptom of colorectal cancer.

Biomarkers

The present inventors have shown that determining the presence and/or level of least two biomarkers in a sample from a subject allows for the detection or diagnosis of colorectal cancer, either early detection at Dukes Stage A or at some later stage such as Dukes Stage B or C or D, with specificity and sensitivity comparable to or greater than that achieved with the FOBT. The at least two biomarkers that are useful in the methods of the present invention are selected from IL-8 (interleukin-8), IGFBP2 (insulin-like growth factor binding protein-2), MAC2BP (MAC2-binding protein; scrum protein 90K), M2PK (pyruvate kinase muscle 2, pyruvate kinase 3), IL-13 (interleukin-13), DKK-3 (dickkopf homolog, 3), EpCAM (epithelial cell adhesion molecule), MIP1β (macrophage inflammatory protein 1β, CCL4, MIP1beta), TGFβ1 (transforming growth factor β1, TGFbeta1) and TIMP-1 (tissue inhibitor of metalloproteinase 1). Reference to any of these biomarkers includes reference to all polypeptide and polynucleotide variants such as isoforms and transcript variants as would be known by the person skilled in the art. NCBI accession numbers of representative sequences for each of the biomarkers are provided in Table 1.

TABLE 1

NCBI accession numbers for representative biomarker sequences.

| Biomarker | Representative NCBI Accession Numbers |
| --- | --- |
| IL-8 | NM_000584.2 (SEQ ID NO: 1) |
| IGFBP2 | NM_000597.2 (SEQ ID NO: 2) |
| MAC2BP | NM_005567.3 (SEQ ID NO: 3) |
| M2PK | NM_002654.3; NM_182470.1; NM_182471.1 (SEQ ID NOs: 4-6) |
| IL-13 | NM_002188.2 (SEQ ID NO: 7) |
| DKK-3 | NM_015881.5; NM_013253; NM_001018057.1 (SEQ ID NOs: 8-10) |
| EpCam | NM_002354.2 (SEQ ID NO: 11) |
| MIP1β | NM_002984.2 (SEQ ID NO: 12) |
| TGFβ1 | NM_000660.4 (SEQ ID NO: 13) |
| TIMP-1 | NM_003254.2 (SEQ ID NO: 14) |

Detecting or Diagnosing Colorectal Cancer

It will be apparent from the preceding description that the diagnostic methods of the present invention may involve a degree of quantification to determine levels biomarkers in patient samples. Such quantification is readily provided by the inclusion of appropriate control samples.

In one embodiment, internal controls are included in the methods of the present invention. A preferred internal control is one or more samples taken from one or more healthy individuals.

In the present context, the term "healthy individual" shall be taken to mean an individual who is known not to suffer from colorectal cancer, such knowledge being derived from clinical data on the individual, including, but not limited to, a different diagnostic assay to that described herein.

As will be known to those skilled in the art, when internal controls are not included in each assay conducted, the control may be derived from an established data set.

Data pertaining to the control subjects are preferably selected from the group consisting of:

1. a data set comprising measurements of the presence or level of expression of biomarkers for a typical population of subjects known to have colorectal cancer;

2. a data set comprising measurements of the presence or level of biomarkers for the subject being tested wherein said measurements have been made previously, such as, for example, when the subject was known to be healthy or, in the case of a subject having colorectal cancer, when the subject was diagnosed or at an earlier stage in disease progression;

3. a data set comprising measurements of the presence or level of biomarkers for a healthy individual or a population of healthy individuals; and 4. a data set comprising measurements of the presence or level of biomarkers for a normal individual or a population of normal individuals.

In the present context, the term "typical population" with respect to subjects known to have colorectal cancer shall be taken to refer to a population or sample of subjects diagnosed with colorectal cancer that is representative of the spectrum of colorectal cancer patients. This is not to be taken as requiring a strict normal distribution of morphological or clinicopathological parameters in the population, since some variation in such a distribution is permissible. Preferably, a "typical population" will exhibit a spectrum of colorectal cancer at different stages of disease progression. It is particularly preferred that a "typical population" exhibits the expression characteristics of a cohort of subjects as described herein.

The term "normal individual" shall be taken to mean an individual that does not express a biomarker, or expresses a biomarker at a low level in a sample. As will be known to those skilled in the art, data obtained from a sufficiently large sample of the population will normalize, allowing the generation of a data set for determining the average level of a particular biomarker.

Those skilled in the art are readily capable of determining the baseline for comparison in any diagnostic assay of the present invention without undue experimentation, based upon the teaching provided herein.

Compounds that bind a biomarker when used diagnostically may be linked to a diagnostic reagent such as a detectable label to allow easy detection of binding events in vitro or in vivo. Suitable labels include radioisotopes, dye markers or other imaging reagents for detection and/or localisation of target molecules. Compounds linked to a detectable label can be used with suitable in vivo imaging technologies such as, for example, radiology, fluoroscopy, nuclear magnetic resonance imaging (MRI), CAT-scanning, positron emission tomography (PET), computerized tomography etc.

The diagnostic methods of the present invention are able to diagnose or detect colorectal cancer with a sensitivity and specificity that is at least comparable to FOBT, or greater. As would be understood by the person skilled in the art, sensitivity refers to the proportion of actual positives in the diagnostic test which are correctly identified as having colorectal cancer. Specificity measures the proportion of negatives which are correctly identified as not having colorectal cancer. In one embodiment, the methods of the invention are able to diagnose or detect colorectal cancer with a sensitivity of at least 50%, 60% or 66%, or at least 77%, 80%, 83%, 85%, 86%, 87%, 88%, 89%, 90%, or at least 93%. In another embodiment, the methods of the invention are able to diagnose or detect colorectal cancer with a sensitivity of at least 80%, or at least 85% or at least 90%, or at least 95%.

In one embodiment, the methods of the invention are able to diagnose or detect colorectal cancer with a specificity of at least 75%, 80%, 85%, 90%, 91%, 92%, 93%, 94% or at least 95%.

Advantageously, the methods of the present invention are able to detect colorectal cancer at all of the Dukes Stages with greater sensitivity than the FOBT. In Dukes Stage A, the tumor has penetrated into, but not through, the bowel wall. In Dukes Stage B, the tumor has penetrated through the bowel wall but there is not yet any lymph node involvement. In Dukes Stage C, the cancer involves regional lymph nodes. In Dukes Stage D, there is distant metastasis, for example, to the liver or lung. In one embodiment, the methods of the present invention are able to diagnose or detect colorectal cancer at any Dukes Stage with a sensitivity of at least 80%.

As known to the skilled person, there are other systems for staging cancer that are know in the art. One example is the TMN Classification of Malignant Tumors (TNM) that is used by the American Joint Committee on Cancer (AJCC: Colon and rectum. in Edge et al., eds; AJCC Cancer Staging Manual, 7$^{th}$ ed. New York, N.Y.: Springer, 2010, pp: 143-164). Another example is the Modified Astler-Coller classification (MAC).

Accordingly, the skilled person will appreciate that the Dukes Stages correspond to certain TNM Classifications. For example, Dukes Stage A corresponds to T1, T2, N0 and M0; Dukes Stage B corresponds to T3, T4a, T4b, N0 and M0; and Dukes Stage C corresponds to i) T1-T2, N1/N1c, M0; ii) T1, N2a and M0; iii) T3-T4a, N1/N1c and M0; iv) T2-T3, N2a and M0; v) T1-T2, N2b and M0; vi) T4a, N2a and M0; vii) T3-T4a, N2b and M0; and viii) T4b, N1-N2 and M0. Thus, the skilled person will understand that reference to a Dukes Stage as used herein includes reference to the corresponding TMN classification as known in the art.

Protein Detection Techniques

In one embodiment, biomarker polypeptide is detected in a patient sample, wherein the presence and/or level of the polypeptide in the sample is indicative of colorectal cancer. For example, the method may comprise contacting a biological sample derived from the subject with a compound capable of binding to a biomarker polypeptide, and detecting the formation of complex between the compound and the biomarker polypeptide. The term "biomarker polypeptide" as used herein includes fragments of biomarker polypeptides, including for example, immunogenic fragments and epitopes of the biomarker polypeptide.

In one embodiment, the compound that binds the biomarker is an antibody.

The term "antibody" as used herein includes intact molecules as well as molecules comprising or consisting of fragments thereof, such as, for example Fab, F(ab')2, Fv and scFv, as well as engineered variants including diabodies, triabodies, mini-bodies and single-domain antibodies which are capable of binding an epitopic determinant. Thus, antibodies may exist as intact immunoglobulins, or as modifications in a variety of forms.

In another embodiment, an antibody to a biomarker polypeptide is detected in a patient sample, wherein the presence and/or level of the antibody in the sample is indicative of colorectal cancer.

Preferred detection systems contemplated herein include any known assay for detecting proteins or antibodies in a biological sample isolated from a human subject, such as, for example, SDS/PAGE, isoelectric focussing, 2-dimensional gel electrophoresis comprising SDS/PAGE and isoelectric focussing, an immunoassay, flow cytometry e.g. fluorescence-activated cell sorting (FACS), a detection based system using an antibody or non-antibody compound, such as, for example, a small molecule (e.g. a chemical compound, agonist, antagonist, allosteric modulator, competitive inhibitor, or non-competitive inhibitor, of the protein). In accordance with these embodiments, the antibody or small molecule may be used in any standard solid phase or solution phase assay format amenable to the detection of proteins. Optical or fluorescent detection, such as, for example, using mass spectrometry, MALDI-TOF, biosensor technology, evanescent fiber optics, or fluorescence resonance energy transfer, is clearly encompassed by the present invention. Assay systems suitable for use in high throughput screening of mass samples, e.g. a high throughput spectroscopy resonance method (e.g. MALDI-TOF, electrospray MS or nano-electrospray MS), are also contemplated. Another suitable protein detection technique involves the use of Multiple Reaction Monitoring (MRM) in LC-MS (LC/MRM-MS) (Anderson and Hunter, 2006).

Immunoassay formats are particularly suitable, e.g., selected from the group consisting of, an immunoblot, a Western blot, a dot blot, an enzyme linked immunosorbent assay (ELISA), radioimmunoassay (RIA), enzyme immunoassay. Modified immunoassays utilizing fluorescence resonance energy transfer (FRET), isotope-coded affinity tags (ICAT), matrix-assisted laser desorption/ionization time of flight (MALDI-TOF), electrospray ionization (ESI), biosensor technology, evanescent fiber-optics technology or protein chip technology are also useful.

Nucleic Acid Detection Techniques

Any suitable technique that allows for the qualitative and/or quantitative assessment of the level of a biomarker polynucleotide in a sample may be used. The terms "nucleic acid molecule" or "polynucleotide" as used herein refer to an oligonucleotide, polynucleotide or any fragment thereof.

Comparison may be made by reference to a standard control, or to a control level that is found in healthy tissue. For example, levels of a transcribed gene can be determined by Northern blotting, and/or RT-PCR. With the advent of quantitative (real-time) PCR, quantitative analysis of gene expression can be achieved by using appropriate primers for the gene of interest. The nucleic acid may be labelled and hybridised on a gene array, in which case the gene concentration will be directly proportional to the intensity of the radioactive or fluorescent signal generated in the array.

Methods for direct sequencing of nucleotide sequences are well known to those skilled in the art and can be found for example in Ausubel et al., eds., Short Protocols in Molecular Biology, 3rd ed., Wiley, (1995) and Sambrook et al., Molecular Cloning, 3rd ed., Cold Spring Harbor Laboratory Press, (2001). Sequencing can be carried out by any suitable method, for example, dideoxy sequencing, chemical sequencing or variations thereof. Direct sequencing has the advantage of determining variation in any base pair of a particular sequence.

Other PCR methods that may be used in carrying out the invention include hybridization based PCR detection systems, TaqMan assay (U.S. Pat. No. 5,962,233) and the molecular beacon assay (U.S. Pat. No. 5,925,517).

The nucleic acid may be separated from the sample for testing. Suitable methods will be known to those of skill in the art. For example, RNA may be isolated from a sample to be analysed using conventional procedures, such as are supplied by QIAGEN technology. This RNA is then reverse-transcribed into DNA using reverse transcriptase and the DNA molecule of interest may then be amplified by PCR techniques using specific primers.

Diagnostic procedures may also be performed directly upon patient samples. Hybridisation or amplification assays, such as, for example, Southern or Northern blot analysis, immunohistochemistly, single-stranded conformational polymorphism analysis (SSCP) and PCR analyses are among techniques that are useful in this respect. If desired, target or probe nucleic acid may be immobilised to a solid support such as a microtitre plate, membrane, polystyrene bead, glass slide or other solid phase.

Kits

The present invention provides kits for the diagnosis or detection of colorectal cancer. Such kits may be suitable for detection of nucleic acid species, or alternatively may be for detection of a polypeptide gene product, as discussed above.

For detection of polypeptides, antibodies will most typically be used as components of kits. However, any agent capable of binding specifically to a biomarker gene product will be useful in this aspect of the invention. Other components of the kits will typically include labels, secondary antibodies, substrates (if the gene is an enzyme), inhibitors, co-factors and control gene product preparations to allow the user to quantitate expression levels and/or to assess whether the diagnosis experiment has worked correctly. Enzyme-linked immunosorbent assay-based (ELISA) tests and competitive ELISA tests are particularly suitable assays that can be carried out easily by the skilled person using kit components.

Optionally, the kit further comprises means for the detection of the binding of an antibody to a biomarker polypeptide. Such means include a reporter molecule such as, for example, an enzyme (such as horseradish peroxidase or alkaline phosphatase), a dye, a radionucleotide, a luminescent group, a fluorescent group, biotin or a colloidal particle, such as colloidal gold or selenium. Preferably such a reporter molecule is directly linked to the antibody.

In yet another embodiment, a kit may additionally comprise a reference sample. In one embodiment, a reference sample comprises a polypeptide that is detected by an antibody. Preferably, the polypeptide is of known concentration. Such a polypeptide is of particular use as a standard. Accordingly, various known concentrations of such a polypeptide may be detected using a diagnostic assay described herein.

For detection of nucleic acids, such kits may contain a first container such as a vial or plastic tube or a microtiter plate that contains an oligonucleotide probe. The kits may optionally contain a second container that holds primers. The probe may be hybridisable to DNA whose altered expression is associated with colorectal cancer and the primers are useful for amplifying this DNA. Kits that contain an oligonucleotide probe immobilised on a solid support could also be developed, for example, using arrays (see supplement of issue 21(1) Nature Genetics, 1999).

For PCR amplification of nucleic acid, nucleic acid primers may be included in the kit that are complementary to at least a portion of a biomarker gene as described herein. The set of primers typically includes at least two oligonucleotides, preferably four oligonucleotides, that are capable of specific amplification of DNA. Fluorescent-labelled oligonucleotides that will allow quantitative PCR determination may be included (e.g. TaqMan chemistry, Molecular Beacons). Suitable enzymes for amplification of the DNA, will also be included.

Control nucleic acid may be included for purposes of comparison or validation. Such controls could either be RNA/DNA isolated from healthy tissue, or from healthy individuals, or housekeeping genes such as β-actin or GAPDH whose mRNA levels are not affected by colorectal cancer.

Regression Algorithms and Statistics

In order to develop a panel of biomarkers suitable for diagnosing or detecting colorectal cancer, the present inventors have analysed numerous biomarkers in a statistical model. Such an improvement in the performance of a test is sometimes referred to as the "in-sample" performance. A fair evaluation of a test requires its assessment using out-of-sample subjects, that is, subjects not included in the construction of the initial predictive model. This is achieved by assessing the test performance using cross validation.

Tests for statistical significance include linear and non linear regression, including ANOVA, Kruskal-Wallis, Wilcoxon, Mann-Whitney and odds ratio, Baysian probability algorithms. As the number of biomarkers measured increases however, it can be generally more convenient to use a more sophisticated technique such as Random Forests, simple logistic, Bayes Net to name a few.

For example, Bayesian probability may be adopted. In this circumstance a 10-fold cross-validation can be used to estimate the "out-of-sample" performance of the models in question. For each combination of biomarkers under consideration, the data can be divided randomly into 10 sub-samples, each with similar proportions of healthy subject and subjects at each stage of disease. In turn, each subsample can be excluded, and a logistic model built using the remaining 90% of the subjects. This model can then be used to estimate the probability of cancer for the excluded subsample, providing an estimate of "out-of-sample" performance. By repeating this for the remaining 9 subsamples, "out-of-sample" performance can be estimated from the study data itself. These out-of sample predicted probabilities can then be compared with the actual disease status of the subjects to create a Receiver Operating Characteristic (ROC) Curve, from which the cross-validated sensitivity at 95% specificity may be estimated.

Each estimate of "out-of-sample" performance using cross-validation (or any other method), whilst unbiased, has an element of variability to it. Hence a ranking of models (based on biomarker combinations) can be indicative only of the relative performance of such models. However a set of biomarkers which is capable of being used in a large number of combinations to generate a diagnostic test as demonstrated via "out-of-sample" performance evaluations, almost certainly contains within itself combinations of biomarkers that will withstand repeated evaluation.

Many different combinations can qualify as diagnostic tests which prove useful and cost effective and have acceptable sensitivity for a given specificity. As an example, consider the five biomarkers: IL-8, IGFBP2, MAC2BP, M2PK and DKK-3. A model discriminating subjects with cancer from healthy controls can be as follows:

$$\log\left(\frac{p}{1-p}\right) = \beta_0 + \beta_{IL8}C_{IL8} + \beta_{IGFBP2}C_{IGFBP2} + \beta_{MAC2BP}C_{MAC2BP} + \beta_{M2PK}C_{M2PK} + \beta_{DKK3}C_{DKK3}$$

Here p represents the probability that a person has colorectal cancer. Each $C_i$ is the logarithm of concentration biomarker i in the plasma (or serum) of a person. Each beta ($\beta$) is a coefficient applying to that biomarker in the concentration units in which it is measured—$\beta_0$ is an "offset" or "intercept". This linear logistic model is common to all results presented herein, but is far from the only way in which a combination of biomarker concentrations may be modelled to predict the probability of cancer.

Other non linear or linear logistic algorithms that would be equally applicable include Random Forest, ANOVA, t-Test, Fisher analysis, Support Vector Machine, Linear Models for MicroArray data (LIMMA) and/or Significance Analyses of Microarray Data (SAM), Best First, Greedy Stepwise, Naive Bayes, Linear Forward Selection, Scatter Search, Linear Discriminant Analysis (LDA), Stepwise Logistic Regression, Receiver Operating Characteristic and Classification Trees (CT).

Thus, in light of the teachings of the present specification, the person skilled in the art will appreciate that the sensitivity and specificity of a test for diagnosing colorectal cancer may be modulated by selecting a different combination of the biomarkers as described herein Knowledge-Based Systems It will be apparent from the discussion herein that knowledge-based computer software and hardware for implementing an algorithm also form part of the present invention. Such computer software and/or hardware are useful for performing a method of diagnosing or detecting colorectal cancer according the invention. Thus, the present invention also provides software or hardware programmed to implement an algorithm that processes data obtained by performing the method of the invention via a multivariate analysis to provide a disease score and provide or permit a diagnosis or detection of colorectal cancer and/or determine progression or status of a colorectal cancer or determine whether or not a colorectal cancer has progressed or determine whether or not a subject is responding to treatment for colorectal cancer in accordance with the results of the disease score in comparison with predetermined values.

In one example, a method of the invention may be used in existing knowledge-based architecture or platforms associated with pathology services. For example, results from a method described herein are transmitted via a communications network (e.g. the internet) to a processing system in which an algorithm is stored and used to generate a predicted posterior probability value which translates to the score of disease probability or risk of recurrence or metastasis or responsiveness to treatment which is then forwarded to an end user in the form of a diagnostic or predictive report.

The method of the invention may, therefore, be in the form of a kit or computer-based system which comprises the reagents necessary to detect the concentration of the biomarkers and the computer hardware and/or software to facilitate determination and transmission of reports to a clinician.

The assay of the present invention permits integration into existing or newly developed pathology architecture or platform systems. For example, the present invention contemplates a method of allowing a user to determine the status of a subject with respect to colorectal cancer, the method including:

(a) receiving data in the form of levels at least two biomarkers selected from IL-8, IGFBP2, MAC2BP, M2PK, IL-13, DKK-3, EpCam, MIP1β, TGFβ1, and TIMP-1 in a readily obtained sample, optionally in combination with another marker of colorectal cancer;

(b) processing the subject data via multivariate analysis (for example, regression analysis) to provide a disease score;

(c) determining the status of the subject in accordance with the results of the disease score in comparison with predetermined values; and (d) transferring an indication of the status of the subject to the user via the communications network reference to the multivariate analysis includes an algorithm which performs the multivariate analysis function.

In one embodiment, the method for diagnosing or detecting colorectal cancer of the invention may be performed by taking a blood sample from a patient and determining the presence and/or level of any one or more of the biomarkers as described herein. If desired, the measurements may be made, for example, on a biochip so that a single analysis can be used to measure the presence and/or level of multiple biomarkers. The results of this analysis may then be inputted into a computer program that subjects them to linear regression analysis. The computer could also contain information as to control values or expected ranges, or the clinician, nurse, medical administrator or general practitioner could input such data. This analysis wold then provide a score or likelihood of having colorectal cancer. If a second test for the patient is performed, the regression analysis may indicate a change in the score, thus indicating that the patient's disease has progressed or worsened.

EXAMPLES

Materials and Methods
Patient Samples

A collection of plasma and serum samples was taken and processed from a cohort of colorectal cancer patients (Dukes Stages A-D) that were being treated at several hospitals.

Blood was also collected and processed from a group of about 50 healthy volunteers over the age of 65 and from a group of 15 over the age of 50.

Four separate studies were undertaken with slightly different biomarkers. Study 1 looked at 52 cancer samples and 50 controls, study 2 looked at 55 cancer samples and 53 controls, study 3 and 4 looked at 96 cancer samples and 50 controls. In study 2, 3 and 4 the patients were age and gender matched across Dukes Stages, see Table 2 for summary statistics.

TABLE 2

Characteristics of normal volunteers and colorectal cancer patients used in studies 2, 3 and 4.

|  | Controls n = 50 | Cancers n = 96 |
|---|---|---|
| Gender |  |  |
| male | 25 | 48 |
| female | 25 | 48 |
| Mean Age (yr) | 68 | 68 |
| Dukes stage |  |  |
| A |  | 22 |
| B |  | 30 |
| C |  | 30 |
| D |  | 14 |
| Tumour site |  |  |
| colon |  | 73 |
| rectum |  | 17 |
| unknown |  | 6 |
| Proximal (includes caecum, ascending, hepatic flexure and transverse colon) |  | 43 |
| Distal (includes splenic flexure, descending, sigmoid and rectum) |  | 47 |

Biomarker Analysis

Analysis of biomarkers was done with commercial kits and sourced antibodies (DSL, R&D Duoset, Calbiotech, Millipore, Abnova, Genway, Peviva, Schebo, Bender) and using ELISA or Luminex assays.

Statistical Evaluation and Panel Biomarker Modelling

Results for each assay were analysed using the statistical software packages Prism and "R". Individual performance of markers was evaluated using the non-parametric Mann-Whitney t-test and individual receiver operator characteristic (ROC) curves were generated.

Logistic regression and related modelling strategies were used to find combinations of biomarkers that best separated controls and colorectal cancer patients. Four separate studies were performed with the same samples/aliquots. The results of each of these is given below.

Results of Study 1, 2 and 3

Biomarkers chosen to be measured in Study 1 and 2 and 3 are listed in Table 3. Biomarkers in bold were those identified as promising from each study (i.e. they were significantly different in samples from colorectal cancer patients versus control and/or they were identified in panels of combined biomarkers that distinguish colorectal cancer from controls).

TABLE 3

Biomarkers analysed in studies.

| Study 1 | Study 2 | Study 3 |
|---|---|---|
| IGF-I | IGF-BP2 | IGF-BP2 (DSL) |
| IGF-II | IGF-II | IGF-II |
| IGF-BP2 | IGF-BP3 | IFNg |
| IGF-BP3 | Her2 | TNFa |
| BTC | VegFA | IL-10 |
| Amphiregulin | VegFC | IL-6 |
| VegFA | VegFD | GM-CSF |
| VegFC | TIMP-1 | IL-12 |
| VegFD | TIMP-2 | IL-13 |
| MMP-2 | MMP-1 | IL-8 |
| MMP-7 | MMP-2 | IL-4 |
| MMP-9 | MMP-3 | Il-2 |
| TIMP-2 | MMP-7 | IL-1b |
| Her2 | MMP-8 | MMP-1 |
|  | MMP-12 | MMP-2 |
|  | MMP-13 | MMP-3 |
|  | ENA-78 | MMP-7 |
|  | MCP-1 | MMP-8 |
|  | MIP-1beta | MMP-9 |
|  | GM-CSF | ENA-78 |
|  | IFN-gamma | MIP-1alpha |
|  | IL-10 | MIP-1beta |
|  | IL-12 | MCP-1 |
|  | IL-13 | Mac-2BP |
|  | IL-1beta | TIMP-1 |
|  | IL-2 | TIMP-2 |
|  | IL-4 | Gro-alpha |
|  | IL-6 | Tumour M2 pyruvate kinase |
|  | IL-8 | M30-apoptosense |
|  | TNF-alpha | M65 |
|  | Cripto | Trail-R2 |
|  |  | P-cadherin |
|  |  | OPN |
|  |  | Dkk-3 |
|  |  | EpCam |
|  |  | TGFbeta1 |
|  |  | REG IV |
|  |  | CEA |
|  |  | DcR3 |
|  |  | CA19.9 |
|  |  | Amphiregulin |
|  |  | CEACAM6 |
|  |  | VegFA pan |
|  |  | VegFA165b |
|  |  | Spondin-2 |
|  |  | survivin |

Statistical Evaluation and Panel Biomarker Modelling

To find combinations of biomarkers that best separated controls and colorectal cancer patients, forward variable selection with Bayesian Information Criteria to penalize log-likelihood to prevent over-fitting was adopted. To estimate the likely performance of the panel of biomarkers on an independent dataset, "N-Fold" or "leave-one-out" cross validation was used. In this procedure one observation at a time was excluded whilst the entire model fitting algorithm was applied to the remaining observations.

The resulting model was then used to estimate the probability that the excluded observation is a case. This was repeated for each observation in the dataset. In this way each observation in turn acted as an independent test of the model-building algorithm. The resulting dataset consisting of cases and controls each with an "independently predicted" case probability can then be compared with the original model. The ability to choose from numerous biomarkers and weight them appropriately allows a search strategy which optimises performance in regions of interest on the ROC curve. The cost of poor specificity is large numbers of unnecessary colonoscopies.

In study 3, 48 potential biomarkers were evaluated to select a candidate panel of colorectal cancer biomarkers, using block randomization within plates to avoid bias. From this list of 48 only 42 showed measurable levels. Individually 14 biomarkers showed significant difference between controls and CRC as assessed by t-tests; (IGFII, IGFBP2, IL-8, IL-6, MMP-1, MMP-7, s90/Mac2BP, M2PK, EpCam, TIMP-1 (serum and plasma), M65, OPN, TGFβ1, VEGF-pan. As expected, none had sufficient sensitivity or specificity to be useful as a biomarker by itself (not shown). However, using a variety of modelling strategies, including use of logarithmic values, several different panels of biomarkers were found that exceeded the performance of FOBT especially for early to late stage disease.

FIG. 1 shows the results from a 7 biomarker panel which included IL8 (serum), IL-13 (serum), EpCAM (plasma), M2PK (plasma), IGFBP2 (serum) and Mac2BP (serum) and which was cross validated to predict its performance on independent samples.

This 7 biomarker model, which is described at least conceptually as $$\log\left(\frac{p}{1-p}\right) = \beta_0 + \beta_{IL8}C_{IL8} + \beta_{IGFBP2}C_{IGFBP2} + \beta_{MAC2BP}C_{MAC2BP} + \beta_{M2PK}C_{M2PK} + \beta_{DKK3}C_{DKK3}$$

provided good performance at high specificity and was robust under cross validation. The coefficients estimated to give the best model for this biomarker combination in plasma are listed in Table 4. Performance statistics are provided in Table 5. This performance exceeds that quoted for FOBT (sensitivity 65.8%, specificity 95%) (Morikawa et al., 2005).

TABLE 4

Coefficients for the biomarker combination.

| Biomarker | Measured in | Concentration Units | Coefficient |
| --- | --- | --- | --- |
| Intercept | NA | NA | −37.74 |
| IL-8 | serum | pg/mL | 1.07 |
| IL-13 | serum | pg/mL | −0.28 |
| EpCAM | plasma | pg/mL | −0.33 |
| M2PK | plasma | units/mL | 1.40 |
| IGFBP2 | serum | ng/mL | 1.99 |
| Mac2BP | serum | ng/mL | 2.39 |
| MIP1beta | Serum | Pg/ml | −1.19 |

TABLE 5

Performance of the 7 biomarker model and cross-validation.

| | Model estimate | Cross validation |
| --- | --- | --- |
| Area Under the ROC Curve (AUC) | 0.91 | 0.86 |
| Sensitivity at 80% specificity | 0.84 | 0.78 |
| Sensitivity at 90% specificity | 0.81 | 0.69 |

This model was also applied separately to patients from each stage of colorectal cancer (Dukes Stage A, B, C, D) and shown to perform equally well within each stage (FIG. 2). The AUCs were 0.88-0.93 and were almost equally good at discriminating all Stages of colorectal cancer. The model shows the highest sensitivity of 90% at 90% specificity for Stage C and the lowest sensitivity of 73% at 90% specificity for Stage B (Table 6).

TABLE 6

Performance of the Model by Dukes Stage

| | Stage A | Stage B | Stage C | Stage D |
| --- | --- | --- | --- | --- |
| Area Under the ROC Curve (AUC) | 0.89 | 0.88 | 0.93 | 0.91 |
| Sensitivity at 80% specificity | 0.82 | 0.77 | 0.90 | 0.93 |
| Sensitivity at 90% specificity | 0.77 | 0.73 | 0.90 | 0.86 |

Study 4 (Also Referred to as "Study 3 Remeasured")

In study 4, 10 biomarkers were remeasured in the same cohort as Study 3. Blood was collected from 96 colorectal cancer patients and 50 normal subjects (the controls). In this study the focus was on 10 biomarkers, namely IGFBP2, IL8, IL13, Mac2BP, M2PK, Dkk3, EpCam, TGFbeta1, TIMP-1, MIP1beta. Assays were performed as described previously. Both serum and plasma levels of each of the biomarkers were measured and compared with control values.

When modelled in pairs (two markers), a total of 5 pairs (out of a possible 45 combinations selected from the list of 10 biomarkers above) could be shown to produce a sensitivity above 52% at a specificity of 95%. See Table 7 and FIG. 3.

TABLE 7

Biomarker Pairs Producing Useful Screening Tests on Cross-Validation.

| Biomarker 1 | Biomarker 2 | Estimated In-Sample (Test) Sensitivity at 95% Specificity | Estimated Out-of-Sample (Cross-Validated) Sensitivity at 95% Specificity |
| --- | --- | --- | --- |
| M2PK | EpCAM | 58.3% | 58.3% |
| M2PK | IL13 | 56.3% | 57.3% |
| Dkk3 | M2PK | 55.2% | 55.2% |
| M2PK | IL8 | 60.4% | 54.2% |
| M2PK | IGFBP2 | 58.3% | 52.1% |

In analysing combinations of three to ten of the nominated biomarkers, there are 968 possible combinations. The 968 combinations of between 3 and 10 biomarkers consist of the 120 combinations of 3 marker; 210 combinations of 4 markers; 252 combinations of 5 markers; 210 combinations of 6 markers; 120 combinations of 7 markers; 45 combinations of 8 markers; 10 combinations of 9 markers and the single combination that includes all 10 biomarkers. When they were modelled using a linear logistic model, and then tested via 10-fold cross validation, about half of the 968 combinations had a sensitivity of 50% at a specificity of 95%, see FIG. 4 which shows the results for a three biomarker combination. More than half of these combinations would have a specificity of 90% and a sensitivity of 50%.

FIG. 5 shows all 485 of the estimated out-of sample (10-fold cross-validated) ROC curves for tests out of a total possible 968 models based on all possible combinations of 3 to 10 of the biomarkers. Note that many individual segments of the 485 ROC curves are coincident, due to as each horizontal segment represents one control and each vertical segment one case. In this instance 50.1% of the combinations have exceeded the 50% sensitivity, 95% specificity, The best estimated "out-of-sample" performance is a sensitivity of 76% at 95% specificity. Repeating the cross-validation will select a different set of models—the sensitivity of any one combination may vary by 10% at 95% specificity due to random sampling—but result in a similar proportion of useful "useful screening tests". Precise validation of individual models requires repeated experiments and larger sample sizes.

FIG. 6 shows how many of the 485 combinations with 50% sensitivity, 95% specificity, include any given biomarker. At the high end, 432 of the chosen "useful" combinations include M2PK. At the low end 227 of the chosen "useful" combinations include MIP1beta. This high representation of all 10 biomarkers in "useful" models shows the unity and self-complementarity of the selection of these 10 biomarkers.

FIG. 7 to FIG. 11 demonstrate some of the results from this last study (Study 4) for combinations of 5 and 7 biomarkers, including a model where the samples are either from plasma or serum cluster. FIG. 11 demonstrates the validity of the choice of three biomarkers (DKK-3, M2PK and IGFBP2) at different stages of the disease progression. The data indicates that at Stage A if the three markers are used, the test still will achieve a significant sensitivity (64%) at 95% specificity which is comparable to the sensitivity achieved at late stage disease, 79%). That is the biomarker panel of three will pick up early disease states allowing early detection.

Tables 8 to 16 list results from various combinations of various biomarker panel sets. Depending on the linear regression that is used, as well as the cohort control and other factors such as sample derivation and assay kit technique, there may be a variation on the actual figures or order of the markers. Regardless, many of these combinations will achieve good selectivity at high specificities so as to be useful for diagnosing or detecting colorectal cancer at any stage of the disease progression.

TABLE 8

Combination of three biomarkers in serum that equal or exceed 50% sensitivity at 95% specificity.

| BM1 | BM2 | BM3 | Test Sensitivity at 95% Specificity | Cross Validated Sensitivity at 95% Specificity |
|---|---|---|---|---|
| Dkk3 | M2PK | IGFBP2 | 72.9% | 70.8% |
| Dkk3 | M2PK | IL8 | 62.5% | 61.5% |
| M2PK | IL13 | IGFBP2 | 65.6% | 61.5% |
| M2PK | IGFBP2 | EpCAM | 63.5% | 61.5% |
| M2PK | IL8 | IGFBP2 | 65.6% | 60.4% |
| M2PK | IL8 | IL13 | 61.5% | 58.3% |
| M2PK | MIP1beta | IL13 | 55.2% | 57.3% |
| M2PK | IL8 | Mac2BP | 59.4% | 57.3% |
| M2PK | MIP1beta | TGFbeta1 | 57.3% | 56.3% |
| M2PK | IL8 | EpCAM | 64.6% | 56.3% |
| Dkk3 | M2PK | IL13 | 59.4% | 55.2% |
| Dkk3 | M2PK | EpCAM | 56.3% | 55.2% |
| M2PK | MIP1beta | EpCAM | 59.4% | 55.2% |
| M2PK | IL8 | TGFbeta1 | 58.3% | 55.2% |
| M2PK | IL8 | TIMP1 | 57.3% | 55.2% |
| TGFbeta1 | Mac2BP | TIMP1 | 54.2% | 55.2% |
| M2PK | Mac2BP | IGFBP2 | 58.3% | 54.2% |
| Dkk3 | IL8 | Mac2BP | 55.2% | 53.1% |
| M2PK | MIP1beta | Mac2BP | 52.1% | 53.1% |
| M2PK | MIP1beta | IGFBP2 | 57.3% | 53.1% |
| M2PK | TIMP1 | EpCAM | 58.3% | 53.1% |
| M2PK | MIP1beta | IL8 | 56.3% | 52.1% |
| M2PK | IL13 | TIMP1 | 58.3% | 52.1% |
| Dkk3 | M2PK | Mac2BP | 57.3% | 51.0% |
| Dkk3 | M2PK | TIMP1 | 55.2% | 51.0% |
| M2PK | IL13 | Mac2BP | 58.3% | 51.0% |
| M2PK | TGFbeta1 | IGFBP2 | 52.1% | 51.0% |
| M2PK | TGFbeta1 | TIMP1 | 57.3% | 51.0% |
| M2PK | TGFbeta1 | Mac2BP | 56.3% | 50.0% |
| IL8 | IL13 | Mac2BP | 61.5% | 50.0% |
| IL8 | TGFbeta1 | Mac2BP | 53.1% | 50.0% |
| M2PK | MIP1beta | TIMP1 | 49.0% | 49.0% |
| M2PK | TGFbeta1 | EpCAM | 49.0% | 47.9% |
| IL8 | IL13 | IGFBP2 | 49.0% | 47.9% |
| IL8 | Mac2BP | IGFBP2 | 57.3% | 47.9% |

TABLE 8-continued

Combination of three biomarkers in serum that equal or exceed 50% sensitivity at 95% specificity.

| BM1 | BM2 | BM3 | Test Sensitivity at 95% Specificity | Cross Validated Sensitivity at 95% Specificity |
|---|---|---|---|---|
| Dkk3 | M2PK | MIP1beta | 55.2% | 46.9% |
| TGFbeta1 | Mac2BP | IGFBP2 | 46.9% | 46.9% |
| Dkk3 | Mac2BP | IGFBP2 | 49.0% | 45.8% |
| M2PK | IL13 | EpCAM | 50.0% | 45.8% |
| IL8 | Mac2BP | TIMP1 | 52.1% | 45.8% |
| IL13 | Mac2BP | IGFBP2 | 45.8% | 44.8% |
| Dkk3 | IL8 | TGFbeta1 | 41.7% | 43.8% |
| MIP1beta | IL8 | Mac2BP | 42.7% | 43.8% |
| MIP1beta | IL8 | EpCAM | 44.8% | 43.8% |
| IL8 | TGFbeta1 | EpCAM | 46.9% | 43.8% |
| Dkk3 | IL8 | EpCAM | 51.0% | 42.7% |
| IL8 | IGFBP2 | EpCAM | 43.8% | 42.7% |
| M2PK | Mac2BP | TIMP1 | 51.0% | 41.7% |

TABLE 9

Combination of four biomarkers including DKK-3 in serum that equal or exceed 50% sensitivity at 95% specificity.

| BM1 | BM2 | BM3 | BM4 | Test Sensitivity at 95% Specificity | Cross Validated Sensitivity at 95% Specificity |
|---|---|---|---|---|---|
| Dkk3 | M2PK | Mac2BP | IGFBP2 | 68.8% | 69.8% |
| Dkk3 | M2PK | IL8 | IL13 | 71.9% | 68.8% |
| Dkk3 | M2PK | IL8 | EpCAM | 70.8% | 67.7% |
| Dkk3 | M2PK | TGFbeta1 | Mac2BP | 67.7% | 65.6% |
| Dkk3 | M2PK | IL8 | IGFBP2 | 69.8% | 64.6% |
| Dkk3 | M2PK | IL8 | Mac2BP | 69.8% | 63.5% |
| Dkk3 | M2PK | MIP1beta | TGFbeta1 | 65.6% | 61.5% |
| Dkk3 | M2PK | IL8 | TIMP1 | 68.8% | 61.5% |
| Dkk3 | M2PK | IL13 | IGFBP2 | 63.5% | 61.5% |
| Dkk3 | M2PK | MIP1beta | IL8 | 59.4% | 60.4% |
| Dkk3 | M2PK | IGFBP2 | EpCAM | 68.8% | 60.4% |
| Dkk3 | M2PK | MIP1beta | IGFBP2 | 69.8% | 59.4% |
| Dkk3 | M2PK | TGFbeta1 | IGFBP2 | 61.5% | 59.4% |
| Dkk3 | M2PK | IL13 | Mac2BP | 56.3% | 58.3% |
| Dkk3 | M2PK | TGFbeta1 | TIMP1 | 65.6% | 58.3% |
| Dkk3 | M2PK | MIP1beta | IL13 | 57.3% | 57.3% |
| Dkk3 | IL8 | Mac2BP | IGFBP2 | 62.5% | 56.3% |
| Dkk3 | M2PK | IL8 | TGFbeta1 | 65.6% | 55.2% |
| Dkk3 | M2PK | IL13 | TIMP1 | 57.3% | 55.2% |
| Dkk3 | M2PK | Mac2BP | TIMP1 | 57.3% | 55.2% |
| Dkk3 | M2PK | MIP1beta | Mac2BP | 57.3% | 54.2% |
| Dkk3 | IL8 | IL13 | Mac2BP | 61.5% | 54.2% |
| Dkk3 | M2PK | TGFbeta1 | EpCAM | 61.5% | 53.1% |
| Dkk3 | M2PK | IGFBP2 | TIMP1 | 61.5% | 53.1% |
| Dkk3 | M2PK | IL13 | TGFbeta1 | 63.5% | 52.1% |
| Dkk3 | M2PK | TIMP1 | EpCAM | 56.3% | 52.1% |
| Dkk3 | IL8 | Mac2BP | TIMP1 | 57.3% | 52.1% |
| Dkk3 | M2PK | MIP1beta | EpCAM | 60.4% | 51.0% |
| Dkk3 | TGFbeta1 | Mac2BP | TIMP1 | 59.4% | 51.0% |

TABLE 10

Combination of four biomarkers including M2PK in serum that equal or exceed 50% sensitivity at 95% specificity.

| BM1 | BM2 | BM3 | BM4 | Test Sensitivity at 95% Specificity | Cross Validated Sensitivity at 95% Specificity |
|---|---|---|---|---|---|
| M2PK | IL8 | Mac2BP | TIMP1 | 63.5% | 65.6% |
| M2PK | Mac2BP | IGFBP2 | EpCAM | 70.8% | 65.6% |

TABLE 10-continued

Combination of four biomarkers including M2PK in serum that equal or exceed 50% sensitivity at 95% specificity.

| BM1 | BM2 | BM3 | BM4 | Test Sensitivity at 95% Specificity | Cross Validated Sensitivity at 95% Specificity |
|---|---|---|---|---|---|
| M2PK | IL8 | IL13 | Mac2BP | 66.7% | 64.6% |
| M2PK | IL8 | TGFbeta1 | Mac2BP | 65.6% | 64.6% |
| M2PK | MIP1beta | IL13 | IGFBP2 | 64.6% | 62.5% |
| M2PK | IL8 | IL13 | TIMP1 | 64.6% | 62.5% |
| M2PK | IL8 | IL13 | EpCAM | 65.6% | 62.5% |
| M2PK | IL13 | Mac2BP | IGFBP2 | 69.8% | 62.5% |
| M2PK | MIP1beta | IL8 | IL13 | 63.5% | 61.5% |
| M2PK | IL8 | Mac2BP | EpCAM | 65.6% | 61.5% |
| M2PK | IL13 | IGFBP2 | EpCAM | 69.8% | 61.5% |
| M2PK | MIP1beta | IL8 | TGFbeta1 | 58.3% | 58.3% |
| M2PK | IL8 | IL13 | IGFBP2 | 67.7% | 58.3% |
| M2PK | IL8 | Mac2BP | IGFBP2 | 61.5% | 58.3% |
| M2PK | IL8 | IGFBP2 | EpCAM | 64.6% | 58.3% |
| M2PK | IL13 | TGFbeta1 | IGFBP2 | 64.6% | 58.3% |
| M2PK | IL13 | TGFbeta1 | EpCAM | 62.5% | 58.3% |
| M2PK | IL13 | IGFBP2 | TIMP1 | 62.5% | 58.3% |
| M2PK | TGFbeta1 | Mac2BP | TIMP1 | 62.5% | 58.3% |
| M2PK | TGFbeta1 | IGFBP2 | EpCAM | 61.5% | 58.3% |
| M2PK | MIP1beta | IL13 | TIMP1 | 57.3% | 57.3% |
| M2PK | MIP1beta | TGFbeta1 | TIMP1 | 58.3% | 57.3% |
| M2PK | MIP1beta | IGFBP2 | EpCAM | 65.6% | 57.3% |
| M2PK | MIP1beta | IL8 | Mac2BP | 54.2% | 56.3% |
| M2PK | IL8 | IL13 | TGFbeta1 | 64.6% | 56.3% |
| M2PK | IL8 | TIMP1 | EpCAM | 62.5% | 56.3% |
| M2PK | IL13 | Mac2BP | TIMP1 | 57.3% | 56.3% |
| M2PK | TGFbeta1 | Mac2BP | IGFBP2 | 60.4% | 56.3% |
| M2PK | IGFBP2 | TIMP1 | EpCAM | 63.5% | 56.3% |
| M2PK | MIP1beta | IL8 | TIMP1 | 57.3% | 55.2% |
| M2PK | IL8 | TGFbeta1 | TIMP1 | 57.3% | 55.2% |
| M2PK | MIP1beta | IL13 | Mac2BP | 57.3% | 54.2% |
| M2PK | MIP1beta | IL8 | EpCAM | 62.5% | 53.1% |
| M2PK | MIP1beta | TIMP1 | EpCAM | 59.4% | 52.1% |
| M2PK | IL13 | TGFbeta1 | TIMP1 | 64.6% | 52.1% |
| M2PK | IL13 | Mac2BP | EpCAM | 51.0% | 52.1% |
| M2PK | MIP1beta | IL13 | TGFbeta1 | 57.3% | 51.0% |
| M2PK | MIP1beta | Mac2BP | IGFBP2 | 57.3% | 51.0% |
| M2PK | TGFbeta1 | Mac2BP | EpCAM | 52.1% | 51.0% |
| M2PK | TGFbeta1 | TIMP1 | EpCAM | 59.4% | 51.0% |
| M2PK | MIP1beta | IL8 | IGFBP2 | 52.1% | 50.0% |
| M2PK | Mac2BP | TIMP1 | EpCAM | 52.1% | 50.0% |
| M2PK | MIP1beta | TGFbeta1 | Mac2BP | 63.5% | 49.0% |
| M2PK | MIP1beta | IL13 | EpCAM | 50.0% | 47.9% |
| M2PK | MIP1beta | TGFbeta1 | EpCAM | 53.1% | 47.9% |
| M2PK | IL13 | TGFbeta1 | Mac2BP | 60.4% | 46.9% |
| M2PK | MIP1beta | TGFbeta1 | IGFBP2 | 49.0% | 44.8% |

TABLE 11

Combination of five biomarkers in serum that equal or exceed 50% sensitivity at 95% specificity.

| BM1 | BM2 | BM3 | BM4 | BM5 | Test Sensitivity at 95% Specificity | Cross Validated Sensitivity at 95% Specificity |
|---|---|---|---|---|---|---|
| Dkk3 | M2PK | IL8 | IL13 | Mac2BP | 74.0% | 70.8% |
| Dkk3 | M2PK | IL8 | IL13 | TIMP1 | 71.9% | 70.8% |
| M2PK | TGFbeta1 | Mac2BP | IGFBP2 | EpCAM | 69.8% | 70.8% |
| Dkk3 | M2PK | MIP1beta | IL8 | IL13 | 71.9% | 69.8% |
| Dkk3 | M2PK | MIP1beta | IGFBP2 | EpCAM | 71.9% | 69.8% |
| Dkk3 | M2PK | IL8 | IGFBP2 | EpCAM | 78.1% | 69.8% |
| Dkk3 | M2PK | TGFbeta1 | Mac2BP | IGFBP2 | 68.8% | 69.8% |
| M2PK | MIP1beta | Mac2BP | IGFBP2 | EpCAM | 69.8% | 68.8% |
| Dkk3 | M2PK | IL8 | TGFbeta1 | Mac2BP | 70.8% | 67.7% |
| Dkk3 | M2PK | Mac2BP | IGFBP2 | EpCAM | 70.8% | 67.7% |
| M2PK | MIP1beta | IL8 | IL13 | Mac2BP | 66.7% | 67.7% |
| Dkk3 | M2PK | IL8 | IL13 | IGFBP2 | 70.8% | 66.7% |
| Dkk3 | M2PK | IL13 | TGFbeta1 | IGFBP2 | 68.8% | 66.7% |
| Dkk3 | M2PK | IL13 | IGFBP2 | EpCAM | 66.7% | 66.7% |
| M2PK | IL13 | Mac2BP | IGFBP2 | EpCAM | 71.9% | 66.7% |
| Dkk3 | M2PK | IL8 | IL13 | TGFbeta1 | 69.8% | 65.6% |
| Dkk3 | M2PK | IL8 | Mac2BP | TIMP1 | 67.7% | 65.6% |
| Dkk3 | M2PK | TGFbeta1 | Mac2BP | EpCAM | 66.7% | 65.6% |
| M2PK | IL8 | IL13 | TGFbeta1 | Mac2BP | 71.9% | 65.6% |
| M2PK | IL8 | IL13 | TGFbeta1 | IGFBP2 | 66.7% | 65.6% |
| M2PK | IL8 | TGFbeta1 | Mac2BP | IGFBP2 | 64.6% | 65.6% |
| M2PK | IL8 | TGFbeta1 | Mac2BP | EpCAM | 69.8% | 65.6% |
| Dkk3 | M2PK | MIP1beta | IL8 | IGFBP2 | 66.7% | 64.6% |
| Dkk3 | M2PK | MIP1beta | Mac2BP | IGFBP2 | 70.8% | 64.6% |
| M2PK | MIP1beta | IL8 | IL13 | TIMP1 | 65.6% | 64.6% |
| M2PK | MIP1beta | IL8 | TGFbeta1 | Mac2BP | 65.6% | 64.6% |
| M2PK | IL8 | IL13 | Mac2BP | EpCAM | 76.0% | 64.6% |
| M2PK | IL8 | IL13 | IGFBP2 | EpCAM | 72.9% | 64.6% |
| M2PK | IL8 | TGFbeta1 | Mac2BP | TIMP1 | 64.6% | 64.6% |
| M2PK | IL8 | Mac2BP | IGFBP2 | EpCAM | 71.9% | 64.6% |
| Dkk3 | M2PK | IL13 | TGFbeta1 | TIMP1 | 68.8% | 63.5% |
| Dkk3 | M2PK | IGFBP2 | TIMP1 | EpCAM | 67.7% | 63.5% |
| M2PK | MIP1beta | IL13 | IGFBP2 | EpCAM | 67.7% | 63.5% |
| M2PK | IL13 | TGFbeta1 | Mac2BP | IGFBP2 | 66.7% | 63.5% |
| M2PK | IL13 | TGFbeta1 | IGFBP2 | EpCAM | 70.8% | 63.5% |
| Dkk3 | M2PK | MIP1beta | IL13 | TGFbeta1 | 69.8% | 62.5% |

TABLE 11-continued

Combination of five biomarkers in serum that equal or exceed 50% sensitivity at 95% specificity.

| BM1 | BM2 | BM3 | BM4 | BM5 | Test Sensitivity at 95% Specificity | Cross Validated Sensitivity at 95% Specificity |
|---|---|---|---|---|---|---|
| Dkk3 | M2PK | IL8 | IL13 | EpCAM | 65.6% | 62.5% |
| Dkk3 | M2PK | IL8 | TGFbeta1 | IGFBP2 | 70.8% | 62.5% |
| Dkk3 | M2PK | IL8 | Mac2BP | IGFBP2 | 69.8% | 62.5% |
| Dkk3 | M2PK | IL13 | TGFbeta1 | Mac2BP | 68.8% | 62.5% |
| Dkk3 | M2PK | TGFbeta1 | Mac2BP | TIMP1 | 68.8% | 62.5% |
| Dkk3 | M2PK | TGFbeta1 | TIMP1 | EpCAM | 67.7% | 62.5% |
| M2PK | IL8 | IL13 | Mac2BP | TIMP1 | 64.6% | 62.5% |
| M2PK | IL8 | IL13 | IGFBP2 | TIMP1 | 66.7% | 62.5% |
| M2PK | IL13 | IGFBP2 | TIMP1 | EpCAM | 68.8% | 62.5% |
| Dkk3 | M2PK | MIP1beta | IL13 | IGFBP2 | 63.5% | 61.5% |
| Dkk3 | M2PK | IL8 | TGFbeta1 | TIMP1 | 64.6% | 61.5% |

TABLE 12

Combination of seven biomarkers in serum that equal or exceed 50% sensitivity at 95% specificity.

| BM1 | BM2 | BM3 | BM4 | BM5 | BM6 | BM7 | Test Sensitivity at 95% Specificity | Cross Validated Sensitivity at 95% Specificity |
|---|---|---|---|---|---|---|---|---|
| Dkk3 | M2PK | IL8 | Mac2BP | IGFBP2 | TIMP1 | EpCAM | 78% | 56% |
| Dkk3 | M2PK | MIP1beta | IL8 | Mac2BP | IGFBP2 | EpCAM | 76% | 64% |
| Dkk3 | M2PK | IL8 | IL13 | Mac2BP | IGFBP2 | TIMP1 | 73% | 69% |
| Dkk3 | M2PK | IL8 | TGFbeta1 | Mac2BP | IGFBP2 | TIMP1 | 72% | 68% |
| Dkk3 | M2PK | IL8 | TGFbeta1 | Mac2BP | IGFBP2 | EpCAM | 71% | 62% |
| Dkk3 | M2PK | MIP1beta | IL8 | Mac2BP | IGFBP2 | TIMP1 | 70% | 64% |
| Dkk3 | M2PK | IL8 | IL13 | Mac2BP | IGFBP2 | EpCAM | 70% | 67% |
| Dkk3 | M2PK | IL8 | IL13 | TGFbeta1 | Mac2BP | IGFBP2 | 69% | 66% |
| M2PK | MIP1beta | IL8 | Mac2BP | IGFBP2 | TIMP1 | EpCAM | 69% | 55% |
| Dkk3 | M2PK | MIP1beta | IL8 | IL13 | Mac2BP | IGFBP2 | 67% | 68% |
| Dkk3 | M2PK | MIP1beta | IL8 | TGFbeta1 | Mac2BP | IGFBP2 | 67% | 64% |
| Dkk3 | M2PK | MIP1beta | TGFbeta1 | Mac2BP | IGFBP2 | TIMP1 | 65% | 59% |
| Dkk3 | M2PK | IL8 | IL13 | TGFbeta1 | IGFBP2 | TIMP1 | 65% | 52% |
| Dkk3 | M2PK | IL8 | TGFbeta1 | IGFBP2 | TIMP1 | EpCAM | 64% | 56% |
| Dkk3 | M2PK | IL13 | TGFbeta1 | Mac2BP | IGFBP2 | TIMP1 | 64% | 57% |
| M2PK | MIP1beta | IL8 | IL13 | IGFBP2 | TIMP1 | EpCAM | 64% | 50% |
| Dkk3 | M2PK | MIP1beta | IL8 | IL13 | Mac2BP | TIMP1 | 63% | 55% |
| Dkk3 | M2PK | MIP1beta | IL8 | TGFbeta1 | IGFBP2 | EpCAM | 63% | 58% |
| Dkk3 | M2PK | MIP1beta | IL13 | TGFbeta1 | Mac2BP | IGFBP2 | 63% | 53% |
| Dkk3 | M2PK | IL8 | IL13 | TGFbeta1 | Mac2BP | TIMP1 | 63% | 59% |
| M2PK | MIP1beta | IL8 | TGFbeta1 | Mac2BP | IGFBP2 | EpCAM | 63% | 59% |
| Dkk3 | M2PK | MIP1beta | IL8 | TGFbeta1 | Mac2BP | TIMP1 | 62% | 51% |
| Dkk3 | M2PK | MIP1beta | IL8 | IGFBP2 | TIMP1 | EpCAM | 62% | 56% |
| Dkk3 | M2PK | MIP1beta | IL13 | Mac2BP | IGFBP2 | TIMP1 | 62% | 39% |
| Dkk3 | M2PK | IL8 | IL13 | TGFbeta1 | TIMP1 | EpCAM | 62% | 43% |
| Dkk3 | M2PK | IL8 | TGFbeta1 | Mac2BP | TIMP1 | EpCAM | 62% | 50% |
| Dkk3 | MIP1beta | IL8 | IL13 | Mac2BP | IGFBP2 | TIMP1 | 62% | 55% |
| Dkk3 | MIP1beta | IL8 | Mac2BP | IGFBP2 | TIMP1 | EpCAM | 62% | 47% |
| M2PK | MIP1beta | IL8 | IL13 | Mac2BP | IGFBP2 | TIMP1 | 62% | 56% |
| M2PK | IL8 | TGFbeta1 | Mac2BP | IGFBP2 | TIMP1 | EpCAM | 62% | 49% |
| Dkk3 | M2PK | IL8 | IL13 | TGFbeta1 | IGFBP2 | EpCAM | 60% | 56% |
| Dkk3 | M2PK | IL13 | TGFbeta1 | Mac2BP | IGFBP2 | EpCAM | 60% | 55% |
| M2PK | MIP1beta | IL8 | IL13 | Mac2BP | IGFBP2 | EpCAM | 60% | 53% |

TABLE 13

Seven biomarker combinations with Sensitivity between 60% and 52%.

| BM1 | BM2 | BM3 | BM4 | BM5 | BM6 | BM7 | Test Sensitivity at 95% Specificity | Cross Validated Sensitivity at 95% Specificity |
|---|---|---|---|---|---|---|---|---|
| Dkk3 | M2PK | MIP1beta | IL8 | IL13 | TGFbeta1 | EpCAM | 59% | 54% |
| Dkk3 | M2PK | MIP1beta | IL8 | IL13 | IGFBP2 | EpCAM | 59% | 52% |
| Dkk3 | M2PK | MIP1beta | IL8 | TGFbeta1 | IGFBP2 | TIMP1 | 59% | 52% |
| Dkk3 | M2PK | TGFbeta1 | Mac2BP | IGFBP2 | TIMP1 | EpCAM | 59% | 47% |
| Dkk3 | MIP1beta | IL8 | IL13 | TGFbeta1 | Mac2BP | IGFBP2 | 59% | 52% |
| Dkk3 | MIP1beta | IL8 | TGFbeta1 | Mac2BP | IGFBP2 | TIMP1 | 59% | 45% |

TABLE 13-continued

Seven biomarker combinations with Sensitivity between 60% and 52%.

| BM1 | BM2 | BM3 | BM4 | BM5 | BM6 | BM7 | Test Sensitivity at 95% Specificity | Cross Validated Sensitivity at 95% Specificity |
|---|---|---|---|---|---|---|---|---|
| Dkk3 | M2PK | MIP1beta | IL8 | IL13 | TGFbeta1 | Mac2BP | 58% | 41% |
| Dkk3 | M2PK | MIP1beta | IL8 | TGFbeta1 | TIMP1 | EpCAM | 58% | 50% |
| Dkk3 | M2PK | IL8 | IL13 | IGFBP2 | TIMP1 | EpCAM | 58% | 55% |
| Dkk3 | MIP1beta | IL8 | IL13 | Mac2BP | IGFBP2 | EpCAM | 58% | 50% |
| Dkk3 | IL8 | IL13 | TGFbeta1 | Mac2BP | IGFBP2 | TIMP1 | 58% | 52% |
| M2PK | IL8 | IL13 | Mac2BP | IGFBP2 | TIMP1 | EpCAM | 58% | 52% |
| Dkk3 | M2PK | MIP1beta | IL13 | TGFbeta1 | IGFBP2 | | 57% | 49% |
| Dkk3 | M2PK | MIP1beta | IL8 | IL13 | TIMP1 | EpCAM | 57% | 48% |
| Dkk3 | M2PK | MIP1beta | IL13 | Mac2BP | IGFBP2 | EpCAM | 57% | 51% |
| Dkk3 | M2PK | MIP1beta | TGFbeta1 | Mac2BP | IGFBP2 | EpCAM | 57% | 46% |
| Dkk3 | M2PK | MIP1beta | TGFbeta1 | IGFBP2 | TIMP1 | EpCAM | 57% | 49% |
| Dkk3 | M2PK | IL13 | Mac2BP | IGFBP2 | TIMP1 | EpCAM | 57% | 49% |
| Dkk3 | MIP1beta | IL8 | TGFbeta1 | Mac2BP | IGFBP2 | EpCAM | 57% | 50% |
| M2PK | MIP1beta | IL8 | IL13 | TGFbeta1 | TIMP1 | EpCAM | 57% | 43% |
| M2PK | IL8 | IL13 | TGFbeta1 | IGFBP2 | TIMP1 | EpCAM | 57% | 52% |
| Dkk3 | M2PK | MIP1beta | Mac2BP | IGFBP2 | TIMP1 | EpCAM | 56% | 47% |
| Dkk3 | IL8 | IL13 | Mac2BP | IGFBP2 | TIMP1 | EpCAM | 56% | 48% |
| MIP1beta | IL8 | IL13 | TGFbeta1 | Mac2BP | IGFBP2 | TIMP1 | 56% | 54% |
| Dkk3 | M2PK | MIP1beta | IL8 | TGFbeta1 | Mac2BP | EpCAM | 55% | 35% |
| Dkk3 | M2PK | MIP1beta | IL13 | IGFBP2 | TIMP1 | EpCAM | 55% | 44% |
| Dkk3 | M2PK | IL8 | IL13 | TGFbeta1 | Mac2BP | EpCAM | 55% | 35% |
| Dkk3 | IL8 | IL13 | TGFbeta1 | Mac2BP | IGFBP2 | EpCAM | 55% | 50% |
| Dkk3 | IL8 | IL13 | TGFbeta1 | IGFBP2 | TIMP1 | EpCAM | 55% | 54% |
| Dkk3 | M2PK | MIP1beta | IL8 | IL13 | Mac2BP | EpCAM | 54% | 49% |
| Dkk3 | M2PK | MIP1beta | IL8 | Mac2BP | TIMP1 | EpCAM | 54% | 39% |
| Dkk3 | M2PK | IL13 | TGFbeta1 | IGFBP2 | TIMP1 | EpCAM | 54% | 42% |
| Dkk3 | IL8 | TGFbeta1 | Mac2BP | IGFBP2 | TIMP1 | EpCAM | 54% | 51% |
| M2PK | MIP1beta | IL8 | IL13 | TGFbeta1 | IGFBP2 | EpCAM | 54% | 37% |
| M2PK | MIP1beta | IL13 | Mac2BP | IGFBP2 | TIMP1 | EpCAM | 54% | 41% |
| M2PK | IL8 | IL13 | TGFbeta1 | Mac2BP | IGFBP2 | TIMP1 | 54% | 43% |
| MIP1beta | IL8 | IL13 | TGFbeta1 | Mac2BP | IGFBP2 | EpCAM | 54% | 42% |
| Dkk3 | M2PK | MIP1beta | IL8 | IL13 | IGFBP2 | TIMP1 | 53% | 52% |
| Dkk3 | M2PK | IL8 | IL13 | Mac2BP | TIMP1 | EpCAM | 53% | 42% |
| M2PK | MIP1beta | IL8 | TGFbeta1 | IGFBP2 | TIMP1 | EpCAM | 53% | 34% |
| M2PK | MIP1beta | IL13 | TGFbeta1 | Mac2BP | IGFBP2 | EpCAM | 53% | 45% |
| | IL8 | IL13 | TGFbeta1 | Mac2BP | IGFBP2 | EpCAM | 53% | 51% |
| MIP1beta | IL8 | IL13 | Mac2BP | IGFBP2 | TIMP1 | EpCAM | 53% | 39% |
| MIP1beta | IL8 | TGFbeta1 | Mac2BP | IGFBP2 | TIMP1 | EpCAM | 53% | 51% |

TABLE 14

Seven biomarker combinations with sensitivity <53%.

| BM1 | BM2 | BM3 | BM4 | BM5 | BM6 | BM7 | Test Sensitivity at 95% Specificity | Cross Validated Sensitivity at 95% Specificity |
|---|---|---|---|---|---|---|---|---|
| M2PK | MIP1beta | IL8 | IL13 | TGFbeta1 | Mac2BP | EpCAM | 52% | 42% |
| Dkk3 | M2PK | MIP1beta | IL13 | TGFbeta1 | IGFBP2 | EpCAM | 51% | 41% |
| Dkk3 | MIP1beta | IL8 | IL13 | TGFbeta1 | TIMP1 | EpCAM | 51% | 35% |
| M2PK | MIP1beta | IL8 | IL13 | TGFbeta1 | IGFBP2 | TIMP1 | 51% | 38% |
| M2PK | MIP1beta | IL8 | TGFbeta1 | Mac2BP | IGFBP2 | TIMP1 | 51% | 30% |
| M2PK | IL13 | TGFbeta1 | Mac2BP | IGFBP2 | TIMP1 | EpCAM | 51% | 37% |
| Dkk3 | M2PK | MIP1beta | IL8 | IL13 | TGFbeta1 | TIMP1 | 50% | 48% |
| Dkk3 | MIP1beta | IL8 | IL13 | TGFbeta1 | Mac2BP | TIMP1 | 50% | 41% |
| Dkk3 | MIP1beta | IL8 | IL13 | TGFbeta1 | IGFBP2 | TIMP1 | 50% | 42% |
| M2PK | MIP1beta | IL8 | IL13 | TGFbeta1 | Mac2BP | IGFBP2 | 50% | 49% |
| M2PK | MIP1beta | IL8 | IL13 | TGFbeta1 | Mac2BP | TIMP1 | 50% | 35% |
| MIP1beta | IL8 | IL13 | TGFbeta1 | IGFBP2 | TIMP1 | EpCAM | 50% | 39% |
| Dkk3 | M2PK | MIP1beta | IL13 | TGFbeta1 | IGFBP2 | TIMP1 | 49% | 44% |
| Dkk3 | MIP1beta | IL8 | IL13 | TGFbeta1 | Mac2BP | EpCAM | 49% | 33% |
| M2PK | IL8 | IL13 | TGFbeta1 | Mac2BP | TIMP1 | EpCAM | 49% | 43% |
| Dkk3 | M2PK | MIP1beta | IL13 | Mac2BP | TIMP1 | EpCAM | 48% | 43% |
| Dkk3 | MIP1beta | IL8 | IL13 | Mac2BP | TIMP1 | EpCAM | 48% | 38% |
| Dkk3 | MIP1beta | IL8 | TGFbeta1 | Mac2BP | TIMP1 | EpCAM | 48% | 40% |
| Dkk3 | MIP1beta | IL13 | Mac2BP | IGFBP2 | TIMP1 | EpCAM | 48% | 31% |
| Dkk3 | IL8 | IL13 | TGFbeta1 | Mac2BP | TIMP1 | EpCAM | 48% | 38% |
| M2PK | MIP1beta | IL8 | IL13 | Mac2BP | TIMP1 | EpCAM | 48% | 33% |
| M2PK | MIP1beta | IL13 | TGFbeta1 | IGFBP2 | TIMP1 | EpCAM | 48% | 45% |
| M2PK | MIP1beta | TGFbeta1 | Mac2BP | IGFBP2 | TIMP1 | EpCAM | 48% | 37% |

TABLE 14-continued

Seven biomarker combinations with sensitivity <53%.

| BM1 | BM2 | BM3 | BM4 | BM5 | BM6 | BM7 | Test Sensitivity at 95% Specificity | Cross Validated Sensitivity at 95% Specificity |
|---|---|---|---|---|---|---|---|---|
| M2PK | MIP1beta | IL13 | TGFbeta1 | Mac2BP | TIMP1 | EpCAM | 47% | 41% |
| IL8 | IL13 | TGFbeta1 | Mac2BP | IGFBP2 | TIMP1 | EpCAM | 47% | 40% |
| Dkk3 | MIP1beta | IL13 | TGFbeta1 | Mac2BP | IGFBP2 | TIMP1 | 46% | 42% |
| M2PK | MIP1beta | IL8 | TGFbeta1 | Mac2BP | TIMP1 | EpCAM | 46% | 30% |
| Dkk3 | M2PK | MIP1beta | TGFbeta1 | Mac2BP | TIMP1 | EpCAM | 45% | 37% |
| Dkk3 | M2PK | IL13 | TGFbeta1 | Mac2BP | TIMP1 | EpCAM | 45% | 41% |
| Dkk3 | MIP1beta | IL8 | IL13 | TGFbeta1 | IGFBP2 | EpCAM | 45% | 33% |
| Dkk3 | MIP1beta | IL8 | IL13 | IGFBP2 | TIMP1 | EpCAM | 44% | 40% |
| Dkk3 | MIP1beta | IL8 | TGFbeta1 | IGFBP2 | TIMP1 | EpCAM | 44% | 43% |
| Dkk3 | MIP1beta | IL13 | TGFbeta1 | Mac2BP | TIMP1 | EpCAM | 44% | 43% |
| MIP1beta | IL8 | IL13 | TGFbeta1 | Mac2BP | TIMP1 | EpCAM | 44% | 28% |
| Dkk3 | M2PK | MIP1beta | IL13 | TGFbeta1 | Mac2BP | TIMP1 | 43% | 31% |
| Dkk3 | MIP1beta | IL13 | TGFbeta1 | IGFBP2 | TIMP1 | EpCAM | 42% | 40% |
| MIP1beta | IL13 | TGFbeta1 | Mac2BP | IGFBP2 | TIMP1 | EpCAM | 42% | 31% |
| Dkk3 | M2PK | MIP1beta | IL13 | TGFbeta1 | Mac2BP | EpCAM | 41% | 23% |
| Dkk3 | M2PK | MIP1beta | IL13 | TGFbeta1 | TIMP1 | EpCAM | 41% | 33% |
| Dkk3 | MIP1beta | IL13 | TGFbeta1 | Mac2BP | IGFBP2 | EpCAM | 41% | 41% |
| Dkk3 | MIP1beta | TGFbeta1 | Mac2BP | IGFBP2 | TIMP1 | EpCAM | 41% | 39% |
| Dkk3 | IL13 | TGFbeta1 | Mac2BP | IGFBP2 | TIMP1 | EpCAM | 41% | 37% |
| M2PK | MIP1beta | IL13 | TGFbeta1 | Mac2BP | IGFBP2 | TIMP1 | 32% | 27% |

TABLE 15

Sensitivity of nine biomarker combinations in plasma and serum samples at 95% specificity.

| BM1 | BM2 | BM3 | BM4 | BM5 | BM6 | BM7 | BM8 | BM9 | Plasma | Serum |
|---|---|---|---|---|---|---|---|---|---|---|
| Dkk3 | M2PK | MIP1beta | IL8 | IL13 | TGFbeta1 | Mac2BP | IGFBP2 | TIMP1 | 73% | 77% |
| Dkk3 | M2PK | MIP1beta | IL8 | IL13 | TGFbeta1 | Mac2BP | IGFBP2 | EpCAM | 73% | 77% |
| Dkk3 | M2PK | MIP1beta | IL8 | IL13 | TGFbeta1 | Mac2BP | TIMP1 | EpCAM | 54% | 72% |
| Dkk3 | M2PK | MIP1beta | IL8 | IL13 | TGFbeta1 | IGFBP2 | TIMP1 | EpCAM | 58% | 74% |
| Dkk3 | M2PK | MIP1beta | IL8 | IL13 | Mac2BP | IGFBP2 | TIMP1 | EpCAM | 74% | 70% |
| Dkk3 | M2PK | MIP1beta | IL8 | TGFbeta1 | Mac2BP | IGFBP2 | TIMP1 | EpCAM | 71% | 78% |
| Dkk3 | M2PK | MIP1beta | IL13 | TGFbeta1 | Mac2BP | IGFBP2 | TIMP1 | EpCAM | 57% | 72% |
| Dkk3 | M2PK | IL8 | IL13 | TGFbeta1 | Mac2BP | IGFBP2 | TIMP1 | EpCAM | 67% | 76% |
| Dkk3 | MIP1beta | IL8 | IL13 | TGFbeta1 | Mac2BP | IGFBP2 | TIMP1 | EpCAM | 54% | 55% |
| M2PK | MIP1beta | IL8 | IL13 | TGFbeta1 | Mac2BP | IGFBP2 | TIMP1 | EpCAM | 58% | 69% |

TABLE 16

Sensitivity of ten biomarker combinations in plasma and serum samples at 95% specificity.

| BM1 | BM2 | BM3 | BM4 | BM5 | BM6 | BM7 | BM8 | BM9 | BM1o | Plasma | Serum |
|---|---|---|---|---|---|---|---|---|---|---|---|
| Dkk3 | M2PK | MIP1beta | IL8 | IL13 | TGFbeta1 | Mac2BP | IGFBP2 | TIMP1 | EpCAM | 70% | 55% |
| Dkk3 | M2PK | MIP1beta | IL8 | IL13 | TGFbeta1 | Mac2BP | IGFBP2 | TIMP1 | EpCAM | 73% | 68% |

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

The present application claims priority from AU 2010903140, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Anderson and Hunter (2006) Mol Cell Proteomics, 5:573-588.

Cancer in Australia, an overview (2008) AIHW (Australian Institute of Health and Welfare) & AACR (Australasian Association of Cancer Registries), Cancer series no. 46, Cat. No: CAN 42, Canberra: AIHW.

Etzioni et al. (2003) Nat Rev Cancer, 3:243-252.

Hundt et al. (2007) Cancer Epidemiol Biomarkers Prev, 16:1935-1953.

Kimmel (1987) Methods Enzymol, 152:507-511.

Kwoh et al. (1989) Proc Natl Acad Sci USA. 86:1173-1177.

Levin (2004) Gastroenterology, 127:1841-1844.
Lieberman (2010) Gastroenterology, 138:2115-2126.
Morikawa et al. (2005) Gastroenterology, 129:422-428.
Notomi et al. (2000) Nucleic Acids Res. 28:E63.
Tonus (2006) World J Gastroenterol, 12:7007-7011.
Wahl and Berger (1987) Methods Enzymol, 152:399-407.
Walker et al. (1992a) Proc Natl Acad Sci USA. 89:392-396.
Walker et al. (1992b) Nucleic Acids Res. 20:1691-1696.

The invention claimed is:

1. A method for detecting the presence and/or level of protein biomarkers in a subject suspected of having colorectal cancer or a patient having colorectal cancer, the method comprising:
    (a) providing a blood, plasma, or serum sample obtained from the subject or the patient;
    (b) contacting the sample with antibodies that specifically bind protein biomarkers DKK-3 (dickkopf homolog 3), M2PK (pyruvate kinase muscle 2), and IGFBP2 (insulin-like growth factor binding protein-2) in the sample; and
    (c) detecting antibody binding to the protein biomarkers, thereby detecting the presence and/or level of the protein biomarkers.

2. The method of claim 1, wherein the method further comprises contacting the sample with an antibody that specifically binds at least one additional biomarker selected from the group consisting of IGF-I, IGF-II, Amphiregulin, EpCAM, VEGFA, VEGFD, MMP-1, MMP-2, MMP-9, TIMP-1 ENA-78, MCP-1, MIP-1β, IFN-γ, IL-8, IL-10, IL-13, IL-1β, IL-4, IL-6, MAC2BP, M65, OPN, TGFβ-1, and VEGFpan, and detecting antibody binding to the at least one additional biomarker.

3. The method of claim 1, further comprising contacting the antibodies with secondary antibodies that are detectably labelled.

4. The method of claim 1, wherein the subject is suspected of having Dukes Stage A, Stage B, Stage C, or Stage D colorectal cancer, or the patient has Dukes Stage A, Stage B, Stage C, or Stage D colorectal cancer.

5. The method of claim 1, wherein the subject is suspected of having Dukes Stage A colorectal cancer, or the patient has Dukes Stage A colorectal cancer, and the detecting step (c) detects the protein biomarkers in the sample of the subject or the patient with a sensitivity of at least 50% and a specificity of at least 90%.

* * * * *